US012758615B2

(12) United States Patent
Yan et al.

(10) Patent No.: US 12,758,615 B2
(45) Date of Patent: Oct. 13, 2026

(54) COMBINATION THERAPY TO TREAT ERYTHROPOIETIN-RESISTANT ANEMIA IN CHRONIC KIDNEY DISEASE

(71) Applicant: The Chinese University of Hong Kong, Hong Kong (CN)

(72) Inventors: Xiaoyu Yan, Hong Kong (CN); Raymond S.M Wong, Hong Kong (CN); Xiaoqing Fan, An Qing City (CN); Huixi Zou, Hong Kong (CN)

(73) Assignee: The Chinese University of Hong Kong, Hong Kong (CN)

( * ) Notice: Subject to any disclaimer, the term of this patent is extended or adjusted under 35 U.S.C. 154(b) by 460 days.

(21) Appl. No.: 18/538,174

(22) Filed: Dec. 13, 2023

(65) Prior Publication Data

US 2024/0197831 A1 Jun. 20, 2024

Related U.S. Application Data

(60) Provisional application No. 63/387,753, filed on Dec. 16, 2022.

(51) Int. Cl.

| | |
|---|---|
| *A61K 38/19* | (2006.01) |
| *A61K 38/18* | (2006.01) |
| *A61P 7/06* | (2006.01) |

(52) U.S. Cl.

CPC ........ *A61K 38/196* (2013.01); *A61K 38/1816* (2013.01); *A61P 7/06* (2018.01)

(58) Field of Classification Search

None

See application file for complete search history.

(56) References Cited

U.S. PATENT DOCUMENTS

| | | | | |
|---|---|---|---|---|
| 2003/0134795 | A1* | 7/2003 | Farrell | A61K 38/1816 514/7.7 |
| 2016/0176956 | A1* | 6/2016 | Cong | A61K 38/1816 435/375 |
| 2017/0319689 | A1* | 11/2017 | Germaschewski | A61K 39/395 |
| 2018/0118738 | A1* | 5/2018 | Zhou | A61P 19/02 |
| 2020/0369762 | A1* | 11/2020 | Bruederle | C07K 16/245 |
| 2020/0395103 | A1* | 12/2020 | Ramakrishnan | G06F 16/31 |
| 2021/0346464 | A1* | 11/2021 | Laadem | A61K 38/22 |
| 2021/0379154 | A1* | 12/2021 | Tsuji | A61K 38/196 |
| 2022/0016082 | A1* | 1/2022 | Ghalie | A61K 31/706 |
| 2022/0298479 | A1* | 9/2022 | Yamazaki | A61P 7/00 |

OTHER PUBLICATIONS

Santini "Treatment of low-risk myelodysplastic syndromes" Hematology 462-469 (Year: 2016).*

Fan "Fate Determination Role of Erythropoietin and Romiplostim in the Lineage Commitment of Hematopoietic ProgenitorsS" J Pharmacol Exp Ther 382:31-43, Jul. 2022.*

* cited by examiner

*Primary Examiner* — Adam Weidner

(74) *Attorney, Agent, or Firm* — SALIWANCHIK, LLOYD & EISENSCHENK

(57) ABSTRACT

The subject invention pertains to novel methods of treatment for subjects suffering from anemia, particularly as a result of erythropoiesis-stimulating agents (ESAs) resistant anemia. The methods comprise administering at least two compositions to a subject, in which the compositions can comprise a first composition comprising an ESA and a second composition comprising a thrombopoietin receptor agonist (TPO-RA). The combination of ESA with TPO-RA can stimulate the expansion of hematopoietic stem cells.

13 Claims, 11 Drawing Sheets

COMBINATION THERAPY TO TREAT ERYTHROPOIETIN-RESISTANT ANEMIA IN CHRONIC KIDNEY DISEASE

CROSS-REFERENCE TO RELATED APPLICATION

This application claims the benefit of U.S. Ser. No. 63/387,753, filed Dec. 16, 2022, which is hereby incorporated by reference in its entirety including any tables, figures, or drawings.

BACKGROUND OF THE INVENTION

Anemia is a common complication of chronic kidney disease (CKD) and is associated with increased cardiovascular events and hospitalizations. Erythropoietin (EPO) deficiency is considered a primary etiologic factor for renal anemia (Babitt & Lin, 2012). Recombinant human erythropoietin (rHuEPO) has revolutionized anemia management, as it reduces the need for red blood cell (RBC) transfusions and improves anemia-related symptoms and quality of life (Elliott, 2011; Gutti et al., 2016). Despite the great efficacy of rHuEPO, randomized controlled trials have shown that high-dose erythropoiesis-stimulating agents (ESAs) increase the risks of mortality and cardiovascular events (Fukuma et al., 2012; Santos et al., 2011; Zhang, Thamer, Kaufman, Cotter, & Hernin, 2011). Therefore, the United States Food and Drug Administration has recommended that the lowest possible ESA dose be used when treating patients on hemodialysis for end-stage renal disease. In addition, up to 10% of CKD patients with anemia fail to achieve the hemoglobin (Hgb) target after rHuEPO treatment or require large doses of rHuEPO to maintain a target Hgb concentration. These patients are recognized as EPO-resistant or hyporesponsive (Costa et al., 2008) and are typically switched back to blood transfusion, which may lead to poor compliance and associated side effects (Icardi et al., 2013; Kainz, Mayer, Kramar, & Oberbauer, 2010; Kilpatrick et al., 2008; Suttorp et al., 2013).

Therefore, there remains a need for novel and effective approaches to stimulate erythropoiesis, reduce the need for ESA doses and transfusions, and correct EPO-resistance.

BRIEF SUMMARY OF THE INVENTION

The subject invention pertains to novel methods of treatment for subjects suffering from anemia, particularly as a result of erythropoiesis-stimulating agents (ESAs) resistant anemia. In certain embodiments, the novel methods comprise administering a first composition comprising an erythropoiesis-stimulating agent (ESA) and a second composition comprising a thrombopoietin (TPO) receptor agonist (TPO-RA). In preferred embodiments, the TPO-RA is romiplostim, and the ESA is recombinant human erythropoietin (rHuEPO).

In certain embodiments, the ESA administered to the subject can be at a concentration of about 1 IU/kg to about 100000 IU/kg or about 50 IU/kg at least about once per week, twice per week, or, preferably, thrice weekly. In certain embodiments, the TPO-RA is administered at a concentration of about 0.01 μg/kg to about 100 μg/kg or, preferably, about 1 μg/kg at least once about every day, about every week, about every 2 weeks, about every 3 weeks, or, preferably, about every 4 weeks. In certain embodiments, the initial dose of the TPO-RA is administered about 1, about 2, about 3, or about 4 weeks after the initial dose of the ESA.

In certain embodiments, the combination of the ESA with the TPO-RA can stimulate the expansion of hematopoietic stem cells.

DETAILED DISCLOSURE OF THE INVENTION

Selected Definitions

Figure 1:
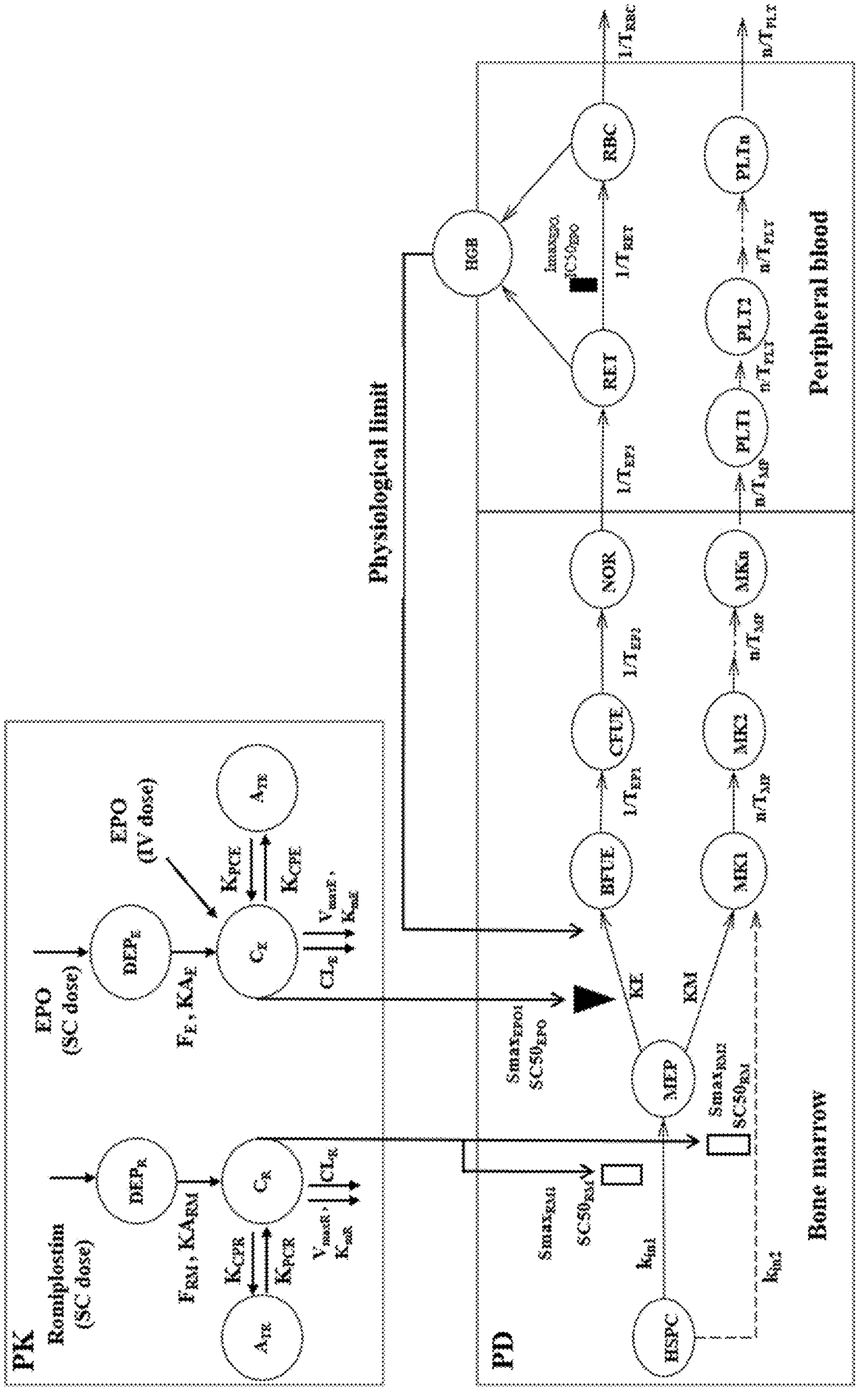
FIG. 1. Schematic diagrams of the proposed PK/PD model of the effects of romiplostim and rHuEPO on RBC and platelet production. Symbols, processes, and model operations are explained in the Materials and Methods section and supplementary materials.

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising". The transitional terms/phrases (and any grammatical variations thereof) "comprising", "comprises", "comprise", "consisting essentially of", "consists essentially of", "consisting" and "consists" can be used interchangeably.

The phrases "consisting essentially of" or "consists essentially of" indicate that the claim encompasses embodiments containing the specified materials or steps and those that do not materially affect the basic and novel characteristic(s) of the claim.

The term "about" means within an acceptable error range for the particular value as determined by one of ordinary skill in the art, which depends in part on how the value is measured, i.e., the limitations of the measurement system. In the context of compositions containing amounts of ingredients where the terms "about" is used, these compositions contain the stated amount of the ingredient with a variation (error range) of 0-10% around the value (X±10%). In other contexts the term "about" is provides a variation (error range) of 0-10% around a given value (X±10%). As is apparent, this variation represents a range that is up to 10% above or below a given value, for example, X±1%, X±2%, X±3%, X±4%, X±5%, X±6%, X 7%, X±8%, X±9%, or X±10%.

In the present disclosure, ranges are stated in shorthand to avoid having to set out at length and describe each and every value within the range. Any appropriate value within the range can be selected, where appropriate, as the upper value, lower value, or the terminus of the range. For example, a range of 0.1-1.0 represents the terminal values of 0.1 and 1.0, as well as the intermediate values of 0.2, 0.3, 0.4, 0.5, 0.6, 0.7, 0.8, 0.9, and all intermediate ranges encompassed within 0.1-1.0, such as 0.2-0.5, 0.2-0.8, 0.7-1.0, etc. Values having at least two significant digits within a range are envisioned, for example, a range of 5-10 indicates all the values between 5.0 and 10.0 as well as between 5.00 and 10.00 including the terminal values. When ranges are used herein, combinations and subcombinations of ranges (e.g., subranges within the disclosed range) and specific embodiments therein are explicitly included.

As used herein, the terms "therapeutically-effective amount," "therapeutically-effective dose," "effective amount," and "effective dose" are used to refer to an amount or dose of a compound or composition that, when administered to a subject, is capable of treating, preventing, or improving a condition, disease, or disorder in a subject. In other words, when administered to a subject, the amount is "therapeutically effective." The actual amount will vary depending on a number of factors including, but not limited to, the particular condition, disease, or disorder being treated, prevented, or improved; the severity of the condition; the weight, height, age, and health of the patient; and the route of administration.

As used herein, the term "treatment" refers to eradicating; reducing; ameliorating; abatement; remission; diminishing of symptoms or delaying the onset of symptoms; slowing in the rate of degeneration or decline; making the final point of degeneration less debilitating; and/or improving a subject's physical or mental well-being or reversing a sign or symptom of a health condition, disease or disorder to any extent, and includes, but does not require, a complete cure of the condition, disease, or disorder. Treating can be curing, improving, or partially ameliorating a disorder. "Treatment" can also include improving or enhancing a condition or characteristic, for example, bringing the function of a particular system in the body to a heightened state of health or homeostasis.

As used herein, "preventing" a health condition, disease, or disorder refers to avoiding, delaying, forestalling, or minimizing the onset of a particular sign or symptom of the condition, disease, or disorder. Prevention can, but is not required, to be absolute or complete; meaning, the sign or symptom may still develop at a later time. Prevention can include reducing the severity of the onset of such a condition, disease, or disorder, and/or inhibiting the progression of the condition, disease, or disorder to a more severe condition, disease, or disorder.

In some embodiments of the invention, the method comprises administration of multiple doses of the compounds of the subject invention. The method may comprise administration of 1, 2, 3, 4, 5, 6, 7, 8, 9, 10, 15, 20, 25, 30, 35, 40, 50, 60, 70, 80, 90, 100 or more therapeutically effective doses of a composition comprising the compounds of the subject invention as described herein. In some embodiments, doses are administered over the course of 1 day, 2 days, 3 days, 4 days, 5 days, 6 days, 7 days, 10 days, 14 days, 21 days, 30 days, 2 months, 3 months, 6 months, 9 months, 1 year, 1.5 years, 2 years, 2.5 years, 5 years or more than 10 years. The frequency and duration of administration of multiple doses of the compositions is such as prevent or treat anemia. Moreover, treatment of a subject with a therapeutically effective amount of the compounds of the invention can include a single treatment or can include a series of treatments. It will also be appreciated that the effective dosage of a compound used for treatment may increase or decrease over the course of a particular treatment. Changes in dosage may result and become apparent from the results of testing for anemia and/or EPO-resistance. In some embodiments of the invention, the method comprises administration of the compounds at several time per day, including but not limiting to 2 times per day, 3 times per day, and 4 times per day.

As used herein, an "isolated" or "purified" compound is substantially free of other compounds. In certain embodiments, purified compounds are at least 60% by weight (dry weight) of the compound of interest. Preferably, the preparation is at least 75%, more preferably at least 90%, and most preferably at least 99%, by weight of the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis.

By "reduces" is meant a negative alteration of at least 1%, 5%, 10%, 25%, 50%, 75%, or 100%.

By "increases" is meant as a positive alteration of at least 1%, 5%, 10%, 25%, 50%, 75%, or 100%.

As used herein, a "pharmaceutical" refers to a compound manufactured for use as a medicinal and/or therapeutic drug.

As used herein, "subject", "host" or "organism" refers to any member of the phylum Chordata, more preferably any member of the subphylum vertebrata, or most preferably, any member of the class Mammalia, including, without limitation, humans and other primates, including non-human primates such as rhesus macaques, chimpanzees and other monkey and ape species; livestock, such as cattle, sheep, pigs, goats and horses; domestic mammals, such as dogs and cats; laboratory animals, including rabbits, mice, rats and guinea pigs; birds, including domestic, wild, and game birds, such as chickens, turkeys, ducks, and geese. The term does not denote a particular age or gender. Thus, adult, young, and new-born individuals are intended to be covered as well as male and female subjects. In some embodiments, a host cell is derived from a subject (e.g., tissue specific cells or stem cells). In some embodiments, the subject is a non-human subject.

Compounds and Methods of Use for Treating ESA Resistant Anemia

Provided are compounds and compositions for treating ESA resistant anemia. Advantageously, the compounds and compositions of the invention comprise administering to a subject an effective amount of a combination of a thrombopoietin (TPO) receptor agonist (TPO-RA) and) and an erythropoiesis-stimulating agent (ESA).

In certain embodiments, the TPO-RA is avatrombopag, eltrombopag, lusutrombopag, romiplostim, recombinant human thrombopoietin (rhTPO), or any combination thereof. In preferred embodiments, the TPO-RA is romiplostim. In certain embodiments, the ESA is erythropoietin (EPO), recombinant human erythropoietin (rHuEPO), darbepoetin, methoxy polyethylene glycol-epoetin beta (Mircera), or any combination thereof. In certain embodiments, the rHuEPO is epoetin alfa, epoetin beta, epoetin zeta, or darbepoetin alfa.

Also provided are methods of using the compounds and compositions of the invention to treat anemia including, but not limited to, ESA resistant anemia in subjects with chronic kidney disease by administering a first composition comprising an ESA and a second composition comprising a TPO-RA to a subject.

In specific embodiments, several applications of the compositions of the invention are administered at specific time intervals. In preferred embodiments, a first and at least one second dose of the first composition are administered with a time interval between doses of about 6 hours, about 12 hours, about 18 hours, about 1 day, about 2 days, about 3 days, about 4 days, about 5 days, about 6 days, about 7 days, about 10 days, about 14 days, about every 3 weeks, about every 4 weeks, about every 6 weeks, every 7 weeks, every 8 weeks, every 9 weeks, every 10 weeks, or longer. In preferred embodiments, a first and at least one second dose of the second composition are administered with a time interval between doses of about 6 hours, about 12 hours, about 18 hours, about 1 day, about 2 days, about 3 days, about 4 days, about 5 days, about 6 days, about 7 days, about 10 days, about 14 days, about every 3 weeks, about every 4 weeks, about every 6 weeks, every 7 weeks, every 8 weeks, every 9 weeks, every 10 weeks, or longer. In certain embodiments, the administration of at least one dose of the first composition and at least one dose the second composition is repeated for a period of at least daily, biweekly, thrice-weekly, weekly, bimonthly, monthly, yearly or at least every about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, about 24 weeks, about 25 weeks, about 26 weeks, or longer.

In some embodiments, a first dose is administered at the same concentration as at least one second dose. In some embodiments a first dose is administered at a different concentration from at least one second dose. In certain embodiments, at least one second dose is administered at a lower concentration than the first dose. In certain embodiments, the at least one second dose of the first composition and/or the at least one second dose of the second composition, should be adjusted, such as, for example, reduced by at least about 1%, about 5%, about 10%, about 15%, about 20%, about 25%, about 30%, about 35%, about 40%, or about 50%. In certain embodiments, the concentration of the first composition and/or the second composition can be adjusted if the hemoglobin concentration in the subject rises rapidly, for example, by >1 g/dL, over about 2 weeks.

The skilled artisan will understand that the dosage of the compositions of the instant invention varies, depending upon, for example, the route of administration, other drugs being administered, and the age, condition, gender and seriousness of the disease in the subject as described above. An effective dose of a TPO-RA or composition thereof of the invention generally ranges between about 0.001 μg/kg of body weight and 100 mg/kg of body weight. Examples of such dosage ranges include, but are not limited to, about 0.01 μg/kg to about 1 mg/kg; about 0.1 μg/kg to about 10 μg/kg; about 0.5 μg/kg to about 7.5 μg/kg; about 0.75 μg/kg to about 5 μg/kg; or about 1 μg/kg. An effective dose of the ESA or composition thereof of the invention generally ranges between about 1 IU/kg to about 100000 IU/kg, about 5 IU/kg to about 10000 IU/kg, about 10 IU/kg to about 1000 IU/kg, about 25 IU/kg to about 100 IU/kg, or about 50 IU/kg.

In certain embodiments, the ESA can be administered at a dose of about 0.01 mcg/kg to about 10.00 mcg/kg, about 0.10 mcg/kg to about 5.00 mcg/kg, about 0.45 mcg/kg to about 2.50 mcg/kg, about 0.50 mcg/kg to about 2.00 mcg/kg, about 0.55 mcg/kg to about 1.50 mcg/kg, about 0.60 mcg/kg to about 1.00 mcg/kg, or about 0.60 mcg. In certain embodiments, the darbepoetin, which is one exemplary ESA, starting dose for CKD subjects on dialysis is about 0.45 mcg/kg intravenously or subcutaneously weekly, or about 0.75 mcg/kg intravenously or subcutaneously every 2 weeks. In certain embodiments, the preferred dose of darbepoetin for the subjects with CKD not on dialysis is about 0.45 mcg/kg intravenously or subcutaneously at 4 week intervals. In certain embodiments, the preferred starting dose of darbepoetin for subjects with cancer on chemotherapy is about 2.25 mcg/kg subcutaneously weekly, or 500 mcg subcutaneously every 3 weeks. In certain embodiments, methoxy polyethylene glycol-epoetin beta (Mircera) can be administered by subcutaneous or intravenous injection with a treatment of 0.6 mcg/kg body weight administered once every two weeks. In certain embodiments, the intravenous route is preferred for patients on hemodialysis.

In some embodiments, the therapeutically effective amount of the first composition or the second composition, of the invention can be administered through intravenous or subcutaneous administration or in a form suitable for administration by inhalation or insufflation, including powders and liquid aerosol administration, or by sustained release systems such as semipermeable matrices of solid hydrophobic polymers containing the compounds of the invention. Administration may be also by way of other carriers or vehicles such as patches, micelles, liposomes, vesicles, implants (e.g. microimplants), synthetic polymers, microspheres, nanoparticles, and the like. In certain embodiments, the coordination compound compositions may be administered using a nanoparticle to passage the composition through skin for treating peripheral (close to skin) conditions.

In some embodiments, the at least one compositions of the instant invention may be formulated for parenteral administration e.g., by injection, for example, bolus injection, intravenous administration, or continuous infusion. In addition, the compositions may be presented in unit dose form in ampoules, pre-filled syringes, and small volume infusion or in multi-dose containers with or without an added preservative. The compositions may be in forms of suspensions, solutions, or emulsions in oily or aqueous vehicles. The composition may further contain formulation agents such as suspending, stabilizing and/or dispersing agents. In further embodiments, the active ingredients of the compositions according to the instant invention may be in powder form, obtained by aseptic isolation of sterile solid or by lyophilization from solution for constitution with a suitable vehicle, e.g., sterile, pyrogen-free water, before use.

The subject compositions can further comprise one or more pharmaceutically acceptable carriers, and/or excipients, and can be formulated into preparations, for example, semi-solid or liquid forms, such as solutions or injections.

The term "pharmaceutically acceptable" as used herein means compatible with the other ingredients of a pharmaceutical composition and not deleterious to the recipient thereof.

Carriers and/or excipients according to the subject invention can include any and all solvents, diluents, buffers (such as, e.g., neutral buffered saline, phosphate buffered saline, or optionally Tris-HCl, acetate or phosphate buffers), oil-in-water or water-in-oil emulsions, aqueous compositions with or without inclusion of organic co-solvents suitable for, e.g., IV use, solubilizers (e.g., Polysorbate 65, Polysorbate 80), colloids, dispersion media, vehicles, fillers, chelating agents (e.g., EDTA or glutathione), amino acids (e.g., glycine), proteins, disintegrants, binders, lubricants, wetting agents, emulsifiers, sweeteners, colorants, flavorings, aromatizers, thickeners (e.g. carbomer, gelatin, or sodium alginate), coatings, preservatives (e.g., Thimerosal, benzyl alcohol, polyquaterium), antioxidants (e.g., ascorbic acid, sodium metabisulfite), tonicity controlling agents, absorption delaying agents, adjuvants, bulking agents (e.g., lactose, mannitol) and the like. The use of carriers and/or excipients in the field of drugs and supplements is well known. Except for any conventional media or agent that is incompatible with the target health-promoting substance or with the composition, carrier or excipient use in the subject compositions may be contemplated.

In certain embodiments, the combination of ESA with TPO-RA can stimulate the expansion of hematopoietic stem cells in the subject. In certain embodiments, the ESA can prohibit TPO-RA-induced thrombocytosis via stem cell competition because the platelets and red blood cells share a common progenitor.

Materials and Methods

Michaelis-Menten approximation of target-mediated drug disposition pharmacokinetics (PK) and pharmacodynamics (PD) (PK/PD) model development The mechanism-based PK/PD model structure was described in our previous publication (Fan et al., 2022). The rHuEPO and romiplostim PK parameters in humans were estimated using the target-mediated drug disposition (TMDD) model (Wang et al., 2010; Yan, Ruixo, & Krzyzanski, 2020), whereas the PK model described in our previous publication was a two-compartment model for rHuEPO and one-compartment model for romiplostim (Fan et al., 2022). To adjust the compartmental PK model to the TMDD model for more precise allometric scaling, Michaelis-Menten (M-M) approximation of the TMDD model was incorporated into our mechanism-based PK/PD model. The general structure of the MM-TMDD PK/PD model of rHuEPO and romiplostim is shown in FIG. 1. The PK model for rHuEPO and romiplostim consists of an MM approximation of the TMDD model, assuming quasi-equilibrium. The differential equations for rHuEPO PK after intravenous (IV) or subcutaneous (SC) administration are as follows (Eq. 1-6):

$$\frac{dA_{DEPE}}{dt} = -KA_E \cdot A_{DEPE} \text{ where } A_{DEPE}(0) = F_E * \text{Dose\_SC}_E \tag{1}$$

$$\frac{dA_{CEPO}}{dt} = -KA_E \cdot A_{DEPE} - CL_{EPO} \cdot C_{EPO} - \frac{V_{MEPO} \cdot C_{EPO}}{K_{MEPO} + C_{EPO}} - K_{CPEPO} \cdot V_{CEPO} \cdot C_{EPO} + K_{PCEPO} \cdot A_{PEPO} \text{ where } A_{CEPO}(0) = \text{Dose\_IV}_E \tag{2}$$

$$\frac{dA_{PEPO}}{dt} = K_{CPEPO} \cdot V_{CEPO} \cdot C_{EPO} - K_{PCEPO} \cdot A_{PEPO} \text{ where } A_{PEPO}(0) = 0 \tag{3}$$

$$C_{EPO} = \frac{1}{2} \times \left(C_{TOTE} - R_{TOTE} - k_{MEPO} + \sqrt{(C_{TOT} - R_{TOTE} - k_{MEPO})^2 + 4 \times k_{MEPO} \times C_{TOTE}}\right. \tag{4}$$

$$R_{TOTE} = V_{MEPO} / (V_{CEPO} \times k_{INTE}) \tag{5}$$

$$C_{TOTE} = A_{CEPO} / V_{CEPO} \tag{6}$$

Similarly, the differential equations for romiplostim PK after SC administration are as follows (Eq. 7-12):

$$\frac{dA_{DEPR}}{dt} = -KA_{RM} \cdot A_{DEPR} \text{ where } A_{DEPR}(0) = F_{RM} * \text{Dose\_SC}_{RM} \tag{7}$$

$$\frac{dA_{CRM}}{dt} = KA_{RM} \cdot A_{DEPR} - CL_{RM} \cdot C_{RM} - \frac{V_{MRM} \cdot C_{RM}}{K_{MRM} + C_{RM}} - K_{CPRM} \cdot V_{CRM} \cdot C_{RM} + K_{PCRM} \cdot A_{PRM} \text{ where } A_{CRM}(0) = \text{Dose\_IV}_{RM} \tag{8}$$

$$\frac{dA_{PRM}}{dt} = K_{CPRM} \cdot V_{CRM} \cdot C_{RM} - K_{PCRM} \cdot A_{PRM} \text{ where } A_{PRM}(0) = 0 \tag{9}$$

$$C_{RM} = \frac{1}{2} \times \left(C_{TOTR} - R_{TOTR} - k_{MRM} + \sqrt{(C_{TOTR} - R_{TOTR} - k_{MRM})^2 + 4 \times k_{MRM} \times C_{TOTR}}\right. \tag{10}$$

$$R_{TOTR} = V_{MRM} / (V_{CRM} \times k_{INTR}) \tag{11}$$

$$C_{TOTR} = \frac{A_{CRM}}{V_{CRM}}, \tag{12}$$

where $A_{DEPE}$, $A_{CEPO}$, and $A_{PEPO}$ are the amounts of rHuEPO in the absorption, central, and peripheral compartments, respectively; and $A_{DEPR}$, $A_{CRM}$, and $A_{PRM}$ are the amounts of romiplostim in the absorption, central, and peripheral compartments, respectively. $K_{AE}$ and KARM are the absorption rates of rHuEPO and romiplostim, respectively; $F_E$ and $F_{RM}$ are the bioavailabilities of rHuEPO and romiplostim, respectively; $V_{CEPO}$ and $V_{CRM}$ are the volumes of the central compartments of rHuEPO and romiplostim, respectively; $CL_{EPO}$ and $CL_{RM}$ are the linear clearances of rHuEPO and romiplostim from the central compartment, respectively; and $R_{TOTE}$ and $R_{TOTR}$ represent the total EPO and TPO receptor concentrations, respectively. $V_{MEPO}$ and $K_{MEPO}$ denote the maximum elimination rate and Michaelis constant of rHuEPO, respectively; $V_{MRM}$ and $K_{MRM}$ denote the maximum elimination rate and Michaelis constant of romiplostim, respectively, which were used to describe MM saturable kinetics; $C_{EPO}$ and $C_{RM}$ are the free serum concentrations of rHuEPO and romiplostim at time t, respectively; and $K_{CPEPO}$ and $K_{PCEPO}$ are the intercompartmental rate constants of rHuEPO. $K_{CPRM}$ and $K_{PCRM}$ are the intercompartmental rate constants of romiplostim; and $K_{INTE}$ and $K_{INTR}$ are the rate constants of the EPO-receptor complex and TPO-receptor complex internalization, respectively.

The previously developed PD model, which mimics the process of erythropoiesis and thrombopoiesis from bone marrow progenitor cells (MEPs) to peripheral blood cells (RBCs and platelets), was applied directly (Fan et al., 2022). The model is based on cell lifespan concepts by using the catenary indirect response model (Krzyzanski, Ramakrishnan, & Jusko, 1999). Details about the PD model equations were described in the original publication (see PD model equations section of Materials and Methods).

Allometric Scaling and Validation

To translate the findings for combination therapy in rats to humans and to predict the optimal human dosing regimen, allometric scaling and model-based simulation were performed. Allometric scaling is based on the concept that many physiological processes and organ sizes (θ) tend to obey a power law (Mager et al., 2009):

$$\theta = a \cdot BW^b, \tag{13}$$

where BW represents body weight, and a and b are drug/process coefficients. Allometric scaling has been widely used to predict PK and PD parameters by performing least-squares linear regression to the power-based simple allometric equation.

As human PK models are available for both romiplostim and rHuEPO, they were used to drive PD in simulations directly. A brief description of the PK parameters of rHuEPO after IV or SC injection and romiplostim after SC injection in humans is presented in Table 1 (Wang et al., 2010; Yan et al., 2012; Yan et al., 2020). Allometric scaling of rHuEPO from rats to humans has been investigated and was used in this study (Woo & Jusko, 2007). The PD data of romiplostim for various species were obtained from the literature (Krzyzanski et al., 2013; Wang et al., 2010). The above relationships were established based on the data collected from healthy rats, monkeys, and humans. Then, the PD parameter estimates in rats (Krzyzanski et al., 2013; Zou et al., 2022) were used to calculate the PD parameters in humans according to the relationships. Because of the influence of disease status, it is risky to directly scale PD parameters from rats with CKD to human patients with CKD. The PD parameters in healthy rats from previous publications were used for scaling to predict the combination dosing regimen in healthy humans. The lifespan of each cell population was scaled using the allometric scaling rule. Physiological parameters such as the baseline platelet and RBC values were based on human values (Corrons, Casafont, & Frasnedo, 2021; Gremmel, Frelinger, & Michelson, 2016). System-specific parameters, such as capacity ($S_{max}$) and sensitivity ($SC_{50}$) parameters, were directly adopted from rats and applied to humans because these parameters tend to be similar across species (Mager et al., 2009). Only nominal variability was assigned to the baseline terms $RBC_0$ and $PLT_0$ (10% CV %) (Mager et al., 2009).

TABLE 1

PK parameters of rHuEPO and romiplostim in humans obtained from the literature (Wang et al., 2010; Yan et al., 2012; Yan et al., 2020).

| Parameter (Unit) | Description | Value | Reference |
|---|---|---|---|
| $CL_E$ (L/h) | Clearance of rHuEPO | 0.379 | (Yan et al., |
| $KA_E$ (1/h) | Absorption rate of rHuEPO | 0.0269 | 2012; Yan |
| $F_E$ | Bioavailability of rHuEPO | 0.513 | et al., 2020) |
| $V_{2E}$ (L) | Volume of distribution of the central compartment of rHuEPO | 3.25 | |
| $V_{3E}$ (L) | Volume of distribution of the peripheral compartment of rHuEPO | 1.64 | |
| $Q_E$ (L/h) | Tissue distribution clearance of rHuEPO | 0.0993 | |
| RTOT (IU/L) | Baseline total receptor | 154.7 | |
| $KM_E$ (IU/L) | Michaelis constant of rHuEPO | 48.1 | |
| $KINT_E$ (1/h) | Internalization rate constant of rHuEPO | 0.171 | |
| $KDEG_E$ (1/h) | Degradation rate constant | 0.392 | |
| $CL_R$ (L/h) | Clearance of romiplostim | 0.183 | (Wang et |
| $V_{2R}$ (L) | Volume of distribution of the central compartment of romiplostim | 4.781 | al., 2010) |
| $K_{CPR}$ (1/h) | Intercompartment rate constant of romiplostim | 0.0806 | |
| $K_{PCR}$ (1/h) | Intercompartment rate constant of romiplostim | 0.0148 | |
| $KA_{RM}$ (1/h) | Absorption rate of romiplostim | 0.0254 | |
| $F_{RM}$ | Bioavailability of romiplostim | 0.499 | |
| $KM_R$ (ng/ml) | Michaelis constant of romiplostim | 0.131 | |
| $\xi_R$ (fg/platelet) | Total c-Mpl receptor concentration | 0.0215 | |
| $KINT_R$ (1/h) | Internalization rate constant of romiplostim | 0.173 | |

The scaled model for healthy subjects was validated externally using the human PD data for romiplostim and rHuEPO in the literature (Krzyzanski, Jusko, Wacholtz, Minton, & Cheung, 2005; Ramakrishnan, Cheung, Wacholtz, Minton, & Jusko, 2004; Wang et al., 2010; Yan et al., 2012; Yan et al., 2020).

Model-Based Simulation of rHuEPO IV and Romiplostim SC Administration PD in Humans To predict the optimal combination therapy dosing regimen in humans, the final model was used to simulate the PD profile of rHuEPO IV and romiplostim SC administration. Different dosing regimens of rHuEPO and romiplostim were considered based on the standard treatment of rHuEPO (50 IU/kg thrice weekly [TIW]) and romiplostim (1 μg/kg). Eight dosing regimens of rHuEPO and romiplostim combination therapy (Table 3) were proposed. The primary safety concern when using romiplostim to correct EPO resistance is the risk of thrombosis. The normal platelet range in healthy individuals is 0.15 to $0.35\times10^{12}$/L (Gremmel et al., 2016); therefore, the safety margin of $0.35\times10^{12}$/L for platelets was proposed.

TABLE 3

Model-based prediction summary in the combination therapy group. The dosing regimen for rHuEPO is 50 IU/kg TIW IV for 16 weeks (102 days), and that of romiplostim is 1 μg/kg SC according to the package insert. The criterion for the prediction results is a platelet range within 0.15-0.35 × $10^{12}$/L compared with healthy individuals. QW = once weekly, Q2W = once every two weeks, Q3W = once every three weeks, Q4W = once every four weeks.

| Regimen number | Dosing regimen | Results | Comments |
|---|---|---|---|
| 1 | Romiplostim QW 1 μg/kg for 16 weeks | Platelet count exceeds 0.35 × $10^{12}$/L on day 11 | Unacceptable |
| 2 | Romiplostim 1 μg/kg Q2W from the first week (weeks 1, 3, 5, 7, 9, 11, 13, 15) | Platelet count exceeds 0.35 × $10^{12}$/L on day 11 | Unacceptable |
| 3 | Romiplostim 1 μg/kg Q2W from the second week (weeks 2, 4, 6, 8, 10, 12, 14, 16) | Platelet count exceeds 0.35 × $10^{12}$/L on day 31 | Unacceptable |
| 4 | Romiplostim 1 μg/kg Q3W from the first week (weeks 1, 4, 7, 10, 13, 16) | Platelet count exceeds 0.35 × $10^{12}$/L on day 11 | Unacceptable |
| 5 | Romiplostim 1 μg/kg Q3W from the second week (weeks 2, 5, 8, 11, 14) | Platelet count will not exceed 0.35 × $10^{12}$/L | Acceptable |
| 6 | Romiplostim 1 μg/kg Q2W from the third week (weeks 3, 5, 6, 9, 11, 13, 15) | Platelet count exceeds 0.35 × $10^{12}$/L on day 50 | Unacceptable |
| 7 | Romiplostim 1 μg/kg Q4W from the first week (weeks 1, 5, 9, 13) | Platelet count exceeds 0.35 × $10^{12}$/L on day 11 | Unacceptable |
| 8 | Romiplostim 1 μg/kg Q4W from the second week (weeks 2, 6, 10, 14) | Platelet count will not exceed 0.35 × $10^{12}$/L | Acceptable (Recommended) |

Software

PK/PD model analysis was performed using NONMEM 7.5 (Icon Development Solutions, Ellicott City, MD, USA). The ordinary differential equations were solved using the ADVAN13 subroutine, and the first-order conditional estimation method with interaction was used for all runs. The use of NONMEM was facilitated by Perl-speaks NONMEM (version 4.9.6, see worldwide website: psn.sourceforge.net/dropship). Graphical visualization and model diagnostics were performed using the R program (version 4.1.1, see worldwide website: r-project.org). Mean PD value time profiles for rHuEPO and romiplostim were extracted using WebPlotDigitizer 4.5 (see worldwide website: apps.automeris.io/wpd/).

PD Model Equations

For RBC production, the PD model comprises a series of compartments, including MEPs, BFU-E, CFU-E, normoblasts (NORs), and RETs that eventually develop into RBCs, to mimic erythropoiesis. The stimulatory effect of romiplostim targets the production rate of MEPs, and the differentiation of MEPs into BFU-E cells is controlled by processes with the first-order rate constant KE, which can be stimulated by rHuEPO, as follows (Eq. 14):

$$\frac{dMEP}{dt} = Kin1\cdot\left(1+\frac{Smax_{RM1}\cdot C_{ROM}}{SC50_{RM}+C_{ROM}}\right) - KE\cdot\left(1+\frac{Smax_{EPO}\cdot C_{EPO}}{SC50_{EPO}+C_{EPO}}\right)\cdot MEP\cdot\left(1-\frac{\Delta HGB}{RH}\right)^{GAM} - KM\cdot MEP, \quad (14)$$

where Kin1 is a zero-order rate constant for producing MEPs. $C_{ROM}$ and $C_{EPO}$ are the serum concentrations of romiplostim and rHuEPO at time t, respectively; $S_{ROM1}$ and $Smax_{EPO}$ are the maximal stimuli of romiplostim and rHuEPO, respectively; and $SC50_{RM}$ and $SC50_{EPO}$ are the concentrations of romiplostim and rHuEPO that induce a half-maximum effect, respectively. MEPs differentiate into erythroid and MK lineages according to the first-order rate constants KE and KM, respectively.

$$\left(1-\frac{\Delta HGB}{RH}\right)^{GAM}$$

represent the physiological limit, a homeostatic mechanism to maintain normal body function. ΔHGB=HGB−HGBO, where HGBO represents the baseline HGB concentration. GAM is a power coefficient. RH is the physiological limit of HGB. The highest RH for HGB was fixed at 24 based on a previous multiple-dose rHuEPO (1350 IU/kg) PK/PD study in rats. The overall production rate of HGB then became zero, preventing the response from increasing further.

$$\frac{dBFUE}{dt} = \quad (15)$$

-continued $$KE\cdot\left(1+\frac{S\max_{EPO}\cdot C_{EPO}}{SC50_{EPO}+C_{EPO}}\right)\cdot MEP\cdot\left(1-\frac{\Delta HGB}{RH}\right)^{GAM}-\frac{1}{T_{EP1}}\cdot BFUE$$

$$\frac{dCFUE}{dt}=2^{MCFU}\cdot\frac{1}{T_{EP1}}\cdot BFUE-\frac{1}{T_{EP2}}\cdot CFUE \tag{16}$$

$$\frac{dNOR}{dt}=2^{MNOR}\cdot\frac{1}{T_{EP2}}\cdot CFUE-\frac{1}{T_{EP3}}\cdot NOR \tag{17}$$

$$\frac{dRET}{dt}=\frac{1}{T_{EP3}}\cdot NOR-\frac{1}{T_{RET}}\cdot RET\cdot\left(1-\frac{I\max_{EPO}\cdot C_{EPO}}{IC50_{EPO}+C_{EPO}}\right) \tag{18}$$

$$\frac{dMRBC}{dt}=\frac{1}{T_{RET}}\cdot RET\cdot\left(1-\frac{I\max_{EPO}\cdot C_{EPO}}{IC50_{EPO}+C_{EPO}}\right)-\frac{1}{T_{RBC}}\cdot MRBC, \tag{19}$$

where $2^{MCFU}$ and $2^{MNOR}$ are factors reflecting the number of CFU-E cells that can be produced by one BFU-E and the number of NORs that can be produced by one CFU-E cell, respectively. $T_{EP}$ represents the average time required for precursors to develop into the next cell population. $T_{RET}$ and $T_{RBC}$ represent the mean residence times for RETs and mature RBCs, respectively. $T_{EP}$ was assumed to be equal to $T_{RET}$ to reduce the number of model parameters. rHuEPO can stimulate the early release of immature RETs from BM into peripheral blood; thus, a part of rHuEPO's effect on the distribution of RET maturation times must be attributed to the release of stress RETs. Hence, in our model, the effect of rHuEPO on the age distribution of RETs was written as $$\left(1-\frac{I\max_{EPO}\cdot C_{EPO}}{IC50_{EPO}+C_{EPO}}\right),$$

which is consistent with the mechanism of action and greatly improves the model fit. $I\max_{EPO}$ is the maximal inhibition of rHuEPO on RETs aging rates, and $IC50_{EPO}$ is the serum concentration of rHuEPO that induces half-maximum inhibition. HGB concentrations were derived from the mass of RBCs, which consists of mature RBCs (MRBC) and RETs:

$$RBC=MRBC+RET \tag{20}$$

$$HGB=MCH\cdot RBC/10 \tag{21}$$

where MCH is the mean corpuscular HGB, which was estimated directly from the data. The denominator 10 converts the MCH unit to pg/cell.

For platelet production, MK1 was assumed to be generated at $K_{in2}$ in addition to the MEP differentiation pathway; the effect of romiplostim is incorporated as a stimulus on the production of both MEPs and MK1. The MK-committed progenitor pathway stimulated by romiplostim was included in the Model:

$$\frac{dMK1}{dt}=Kin2\cdot\left(1+\frac{S\max_{RM2}\cdot C_{ROM}}{SC50_{RM}+C_{ROM}}\right)+KM\cdot MEP-\frac{n}{T_{MP}}\cdot MK1 \tag{22}$$

$S_{ROM2}$ is the maximal stimulus of romiplostim on Kin2. A series of aging compartments (MKn, n=10) denoted the MK precursor cells in BM, with the first-order transition rates $n/T_{MP}$. The model equations are as follows:

$$\frac{dMK_i}{dt}=\frac{n}{T_{MP}}\cdot(MK_{i-1}-MK_i)\ i=2,\ldots,n \tag{23}$$

$$\frac{dPLT_1}{dt}=CF\cdot\frac{n}{T_{MP}}\cdot MK_n-\frac{n}{T_{PLT}}\cdot PLT_1 \tag{24}$$

Similarly, PLTn (n=10) represents the platelets in blood with the transition rate nPLT/TPLT:

$$\frac{dPLT_i}{dt}=\frac{n}{T_{PLT}}\cdot(PLT_{i-1}-PLT_i)\ i=2,\ldots,n, \tag{25}$$

where $T_{MP}$ and $T_{PLP}$ denote the mean lifespans of precursor cells and platelets, respectively. CF represents the conversion factor equal to the average number of platelets produced by an MK and was fixed at 4000. The platelets were modeled as the sum of platelet counts in each PLT compartment:

$$PLT=PLT_1+\ldots+PLT_n \tag{26}$$

The secondary parameters and baseline equations defined by the steady-state value can be used to reduce the number of model parameters as follows:

$$RET_0=MRBC\cdot T_{RET}/T_{RBC} \tag{27}$$

$$NOR_0=RET_0\cdot T_{EP3}/T_{RET} \tag{28}$$

$$CFUE_0=RET_0\cdot T_{EP2}/\left(T_{RET}\cdot 2^{MNOR}\right) \tag{29}$$

$$BFUE_0=RET_0\cdot T_{EP2}/\left(T_{RET}\cdot 2^{MNOR}\cdot 2^{MCFU}\right) \tag{30}$$

$$MEP_0=BFUE_0/(T_{EP1}\cdot KE) \tag{31}$$

$$MKn=T_{MP}\cdot PLT_0/(CF\cdot T_{PLT}\cdot 10) \tag{32}$$

$$K_{in1}=MEP_0\cdot(KM+KE) \tag{33}$$

$$K_{in2}=\frac{PLT_0}{CF\cdot T_{PLT}}-MEP_0\cdot KM \tag{34}$$

The interindividual variabilities (IIVs) of fixed-effect parameters were described by the exponential error model:

$$P_i=\theta_i\cdot\exp\left(\eta_{P_i}\right), \tag{35}$$

where $P_i$ is the ith parameter for the individual, $\theta i$ is the typical value (estimated population geometric mean) for $P_i$, and $\eta_{pi}$ is an independent random variable that is normally distributed with zero mean and variance ($\omega_2$). Random effects were added on $PLT_0$ and $RBC_0$, while for other values of $\theta_i$, variances of random effect parameters were fixed to a small value (0.0225, i.e., 15% coefficient of variation [cv]) to improve the expectation-maximization (EM) algorithm efficiency in NONMEM.

The residual variabilities in RBC, PLT, RET, and HGB were added separately. Different residual error models were explored, including an additive error model, a proportional error model, and a combined error (proportional plus additive) model. Eventually, a combined model of residual error was applied and described as:

$$Y_{ij} = \hat{Y}_{ij} \cdot (1 + \varepsilon_1) + \varepsilon_2 \tag{36}$$

where $Y_{ij}$ is the observation of individual i at time $t_j$, $\hat{Y}_{ij}$ is the corresponding model prediction, and $\varepsilon_i$ and $\varepsilon_2$ are assumed to be independent and normally distributed random variables, respectively, with a zero mean and standard deviation (a).

All patents, patent applications, provisional applications, and publications referred to or cited herein are incorporated by reference in their entirety, including all figures and tables, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

Figure 6A:
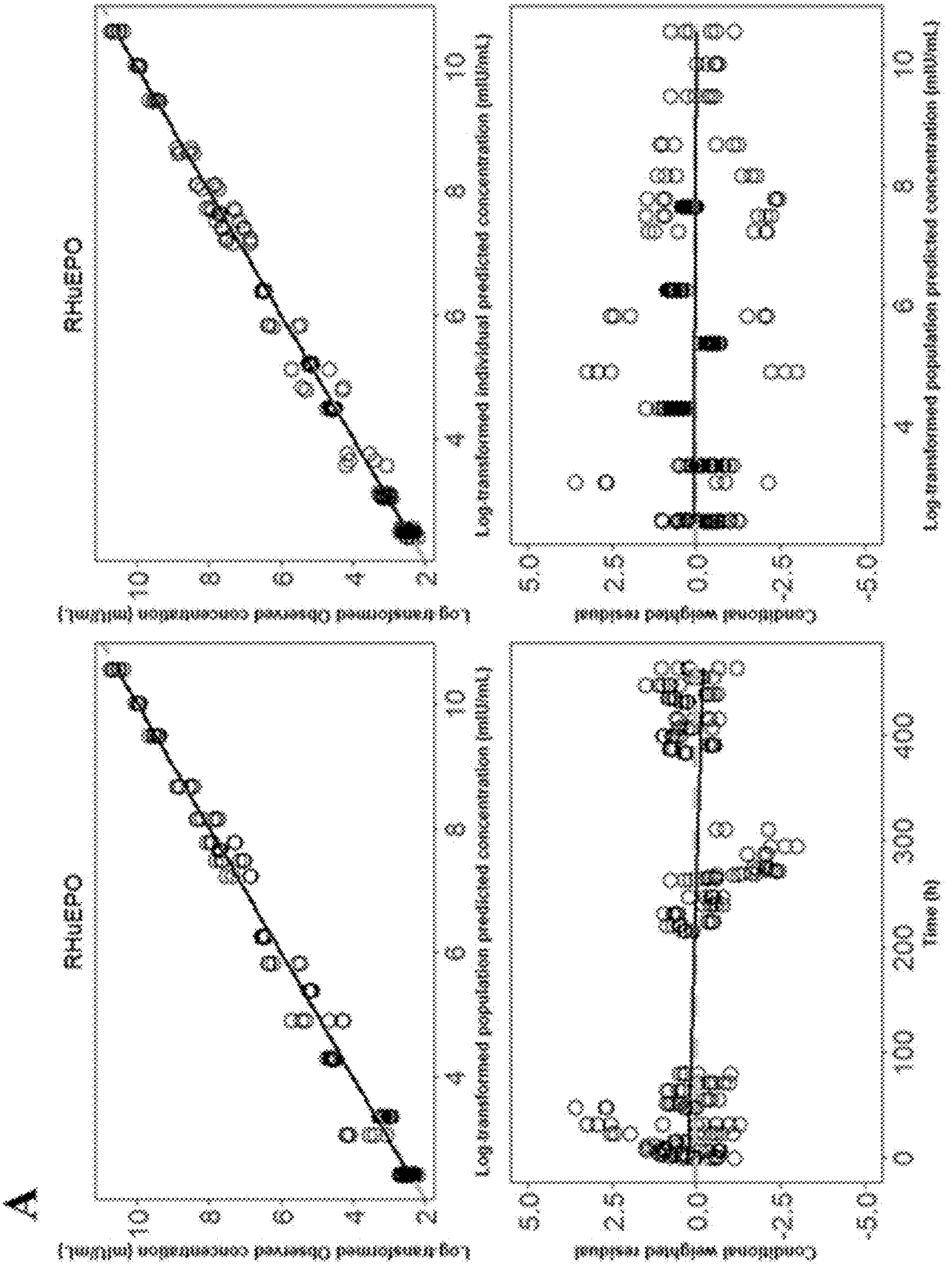
FIGS. 6A-6B. General goodness-of-fit of the final model for rHuEPO (FIG. 6A) and romiplostim (FIG. 6B). The top panels of (FIG. 6A) and (FIG. 6B) present the observed data vs. the population predictions (left) and individual predictions (right), respectively. The bottom panels of (FIG. 6A) and (FIG. 6B) present the conditional weighted residual (CWRES) vs. the time (left) and population predictions (right), respectively. The gray diagonal (top panels of FIGS. 6A-6B) and horizontal (bottom panels of FIGS. 6A-6B) lines are the identity and zero lines, respectively.
Figure 6B:
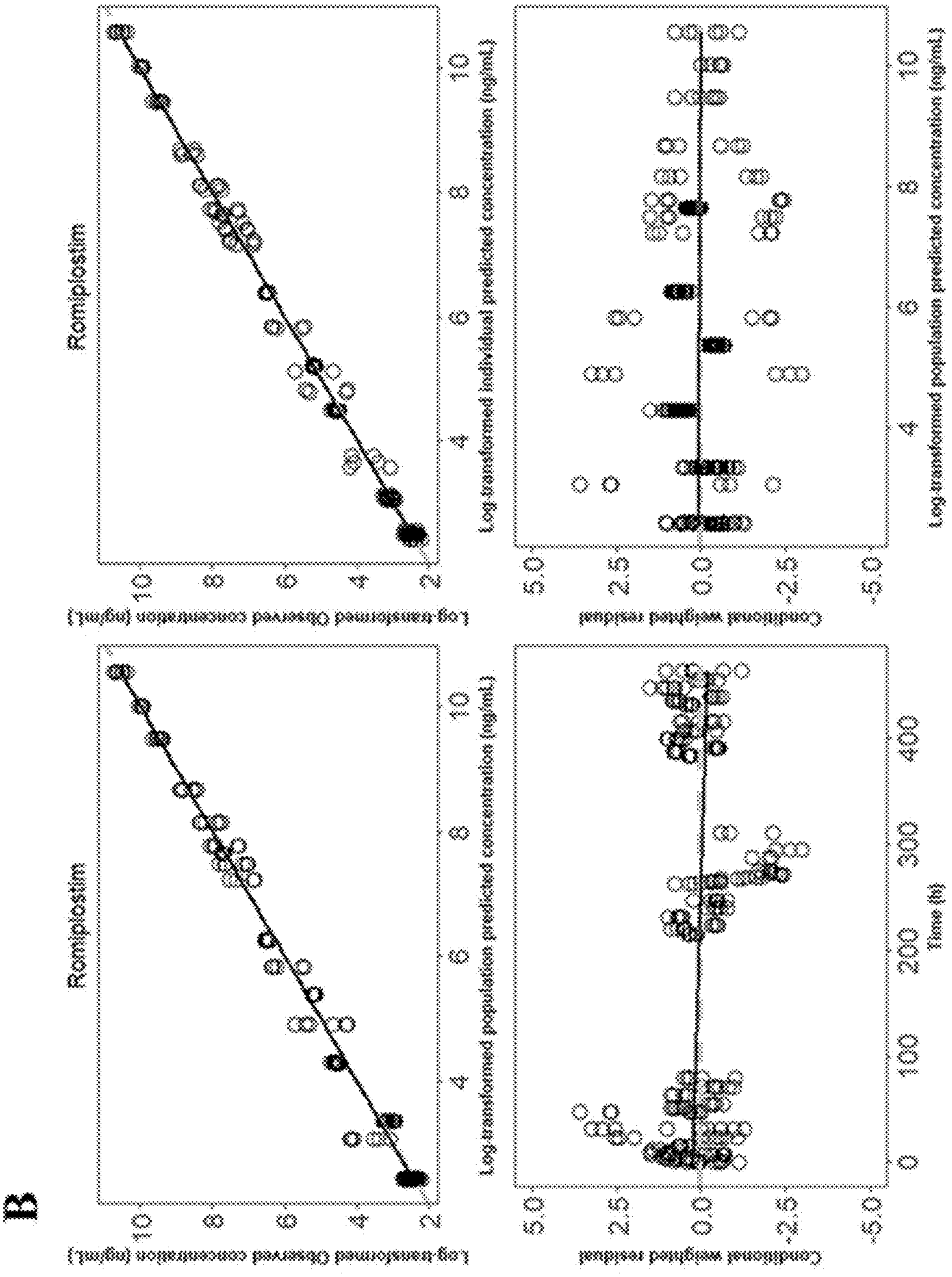
Figure 7A:
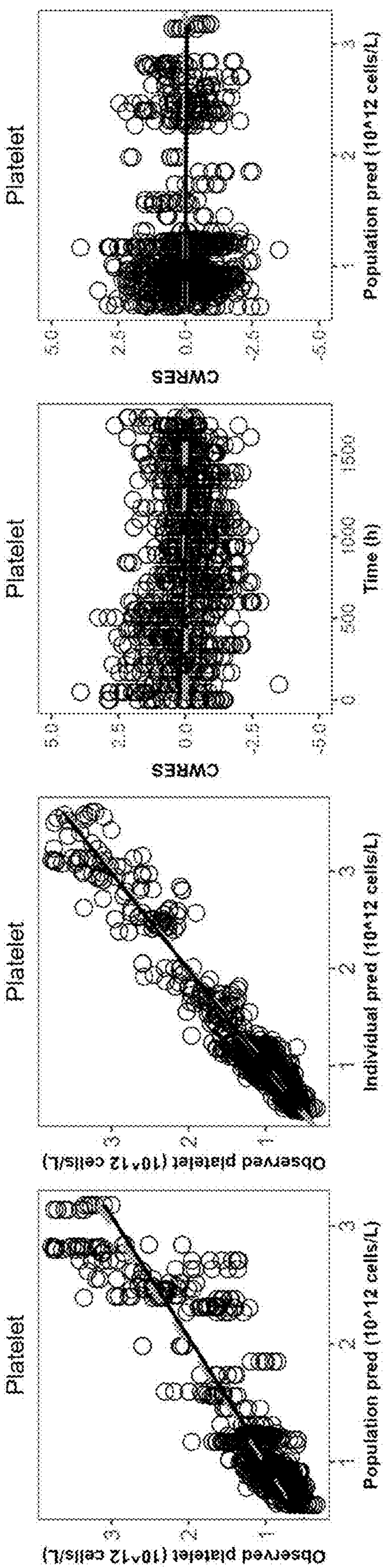
FIGS. 7A-7D. General goodness-of-fit of the final PD model, including platelets (PLT, FIG. 7A), reticulocytes (RETs, FIG. 7B), RBC counts (FIG. 7C), and Hgb concentration (FIG. 7D). Following the left-to-right order, the panels present the observed data vs. population predictions, observed data vs. individual predictions, conditional weighted residual (CWRES) vs. time, and CWRES vs. population predictions, respectively. The gray diagonal and horizontal lines are the identity and zero lines, respectively.
Figure 7B:
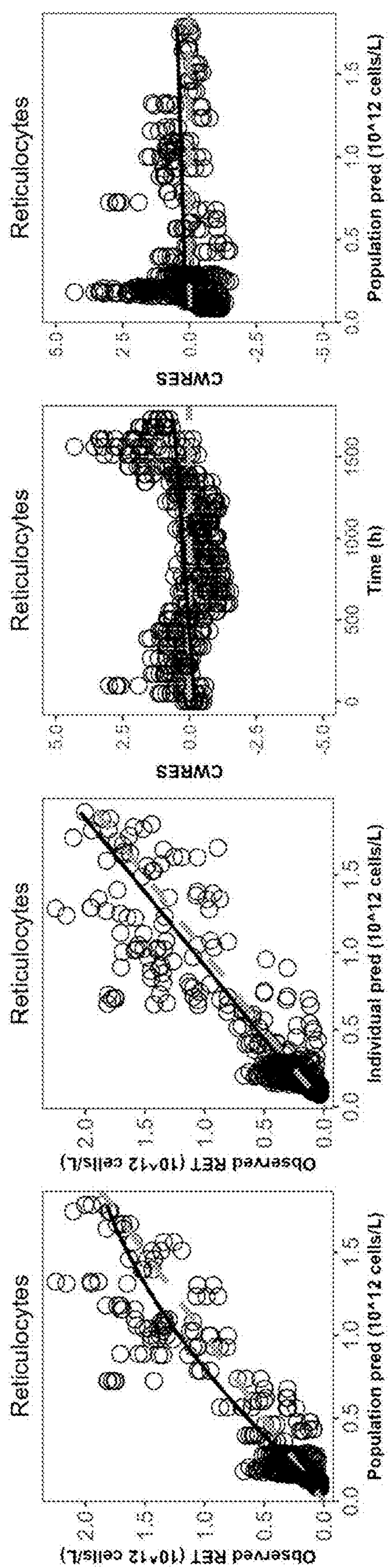
Figure 7C:
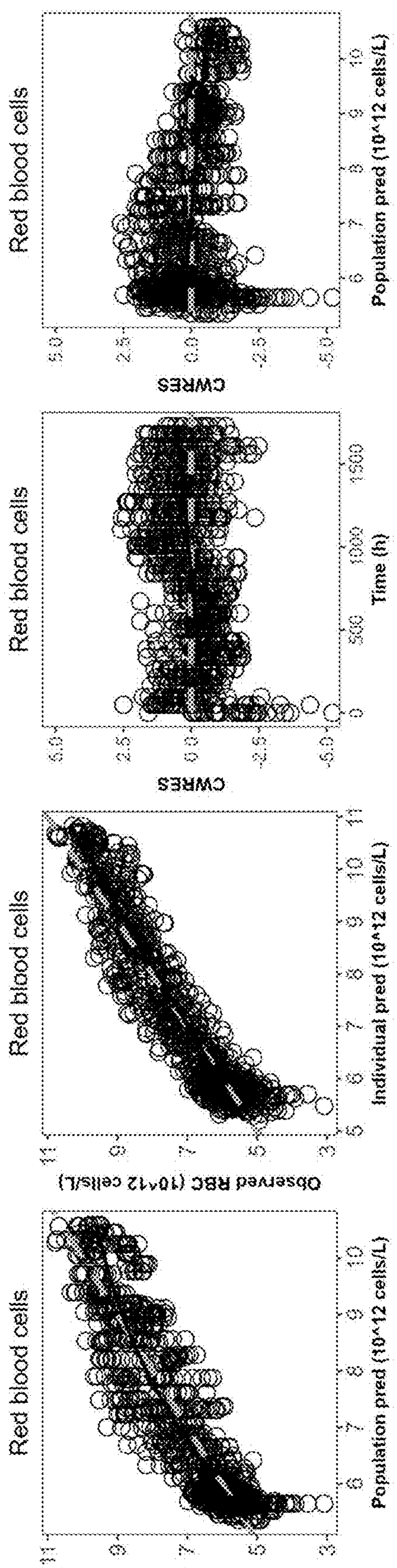
Figure 7D:
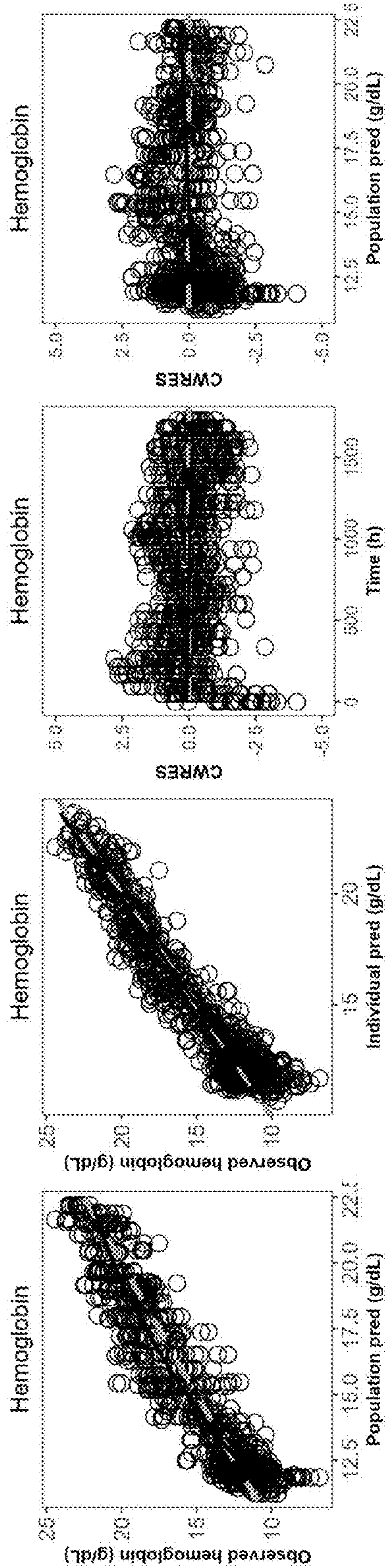

Example 1—M-M Approximation of a Target-Mediated Drug Disposition PK/PD Model Reasonably Characterizes the PK and PD Profiles of Romiplostim and rEuEPO as Monotherapy and Combination Therapy The proposed MM-TMDD PK model captured the concentration-time profiles of romiplostim and rHuEPO after both monotherapy and combination therapy in rats (FIGS. 6A-6B, Table 4. Then, the typical PK parameters obtained from the PK modeling were used to drive the PD model.

The goodness-of-fit diagnostic plots (FIGS. 7A-7D) for the final PD model suggested that the model adequately fitted the PD data in rats. The homogeneous distribution of data points around the identity line presented in the diagnostic plots indicated the absence of systematic bias. The parameter estimates of the model are presented in Supplementary Table S2. All fixed and random effect parameters were adequately estimated, with a relative standard error of less than 50%. The estimates of the hematological parameters $T_{RBC}$ (mean residence times for mature RBCs), $T_{RET}$ (mean residence times for reticulocytes), $T_{MP}$ (mean lifespan of megakaryocyte cells), $T_{PLT}$ (mean lifespan of platelets), $RBC_0$ (baseline RBCs concentration), MCH (mean corpuscular hemoglobin), and $PLT_0$ (baseline platelets in blood) were close to the physiological values (Ait-Oudhia, Scherrmann, & Krzyzanski, 2010; Krzyzanski et al., 2013).

TABLE 4

Model estimates of the fixed- and random-effect PK parameters together with their relative standard errors. IIV = interindividual variability.

| Parameter | Description | Unit | Estimate | % RSE |
|---|---|---|---|---|
| $CL_R$/F | Clearance of romiplostim | L/h/kg | 0.0277 | 5.41 |
| $V_{2R}$/F | Volume of distribution of the central compartment of romiplostim | L/kg | 0.515 | 22.3 |
| $K_{CPR}$/F | Intercompartment rate constant of romiplostim | 1/h | 0.0136 | 79.4 |
| $K_{PCR}$/F | Intercompartment rate constant of romiplostim | 1/h | 0.0493 | 16.5 |
| Ka/F | Absorption rate of romiplostim | 1/h | 0.0917 | 17.5 |
| $K_{mR}$/F | Michaelis constant of romiplostim | μg/L | 10.62 | 6.06 |
| $V_{maxR}$/F | Maximum elimination rate of romiplostim | μg/h/kg | 0.218 | 13.2 |
| $K_{INTR}$/F | Internalization rate constant of romiplostim | 1/h | 0.0279 | 23.4 |
| $\omega_{CL}$ | IIV of $CL_R$/F | Dimensionless | 0.0553 | 26.5 |
| σ of romiplostim | Additive error in logarithmic domain | Dimensionless | 0.112 | 9.49 |
| $CL_E$ | Clearance of rHuEPO | L/h/kg | 0.0135 | 3.06 |
| $V_{2E}$ | Volume of distribution of the central compartment of rHuEPO | L/kg | 0.0293 | 1.64 |
| $K_{CPE}$ | Intercompartment rate constant of rHuEPO | 1/h | 0.180 | 4.31 |
| $K_{PCE}$ | Intercompartment rate constant of rHuEPO | 1/h | 0.196 | 2.90 |
| $K_{mE}$ | Michaelis constant of rHuEPO | IU/L | 7.932 | 2.09 |
| $V_{maxE}$ | Maximum elimination rate of rHuEPO | IU/h/kg | 0.289 | 2.56 |
| $K_{INTE}$ | Internalization rate constant of rHuEPO | 1/h | 0.00173 | 1.02 |
| $\omega_{CLE}$ | IIV of $CL_E$ | Dimensionless | 0.0885 | 79.2 |
| $\omega_{KPCE}$ | IIV of $K_{PCE}$ | Dimensionless | 0.161 | 41.2 |
| σ of rHuEPO | Additive error in logarithmic domain | Dimensionless | 0.195 | 3.33 |

Note:

Relative standard errors (RSE) for ω and σ are reported on the approximate standard deviation scale (standard error/variance estimate)/2.

IIV is expressed as the coefficient of variation (%).

σ represents variance in the residual error.

Example 2—Extrapolation and Validation of the PK/PD Model to Humans

Figure 2A:
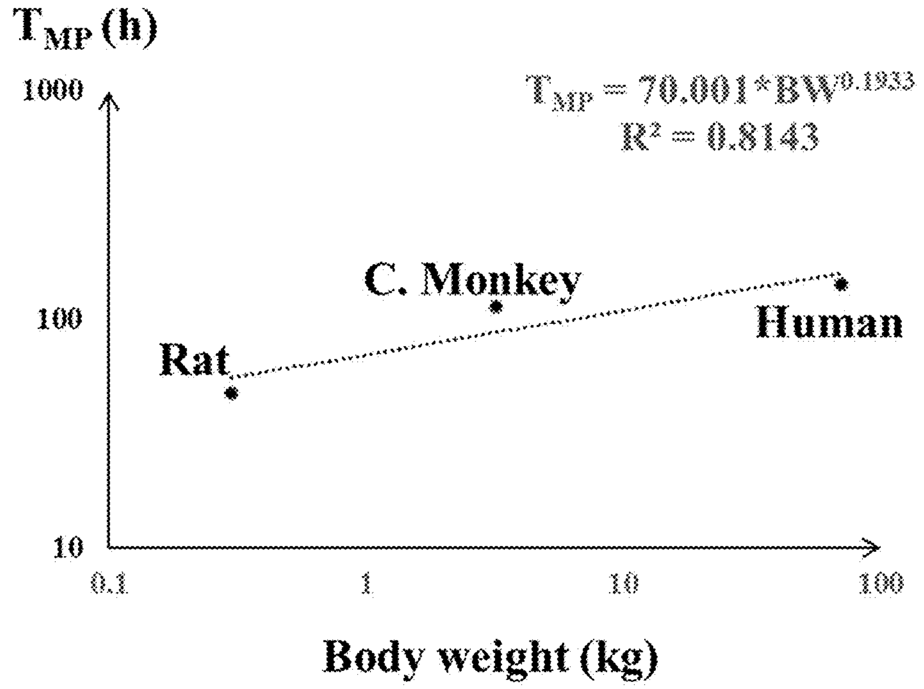
FIGS. 2A-2B. Allometric relationship of the PD parameters $T_{MP}$ (FIG. 2A) and $T_{PLT}$ (FIG. 2B) from rats to humans. A good correlation between body weight and the mean lifespans of megakaryocytes and platelets was observed ($R^2$>0.8). The values of the parameters were obtained from the literature (Wang et al., 2010; Krzyzanski et al., 2013).
Figure 2B:
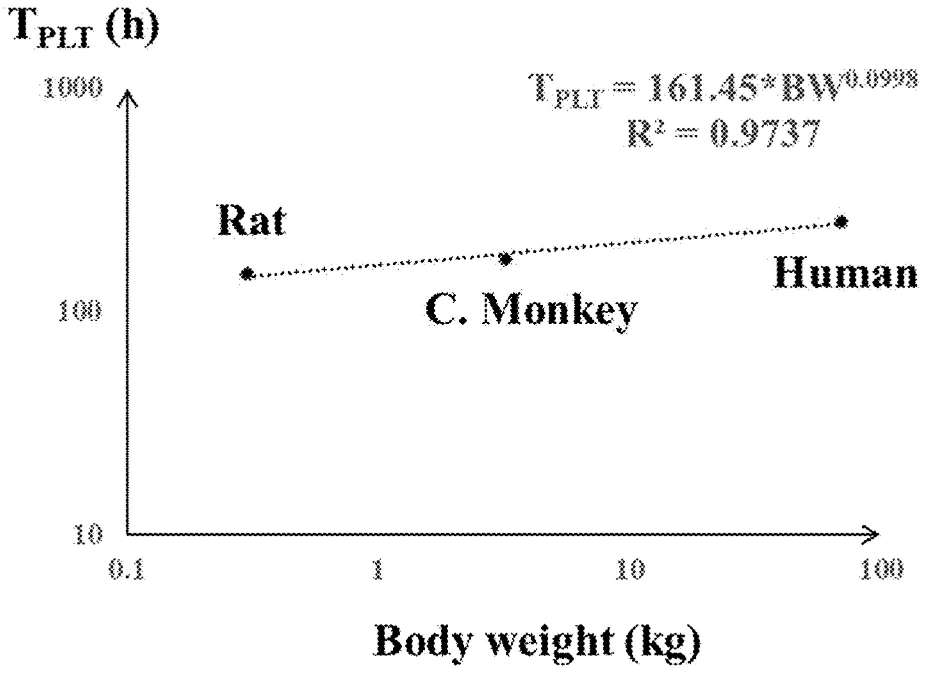
Figure 3A:
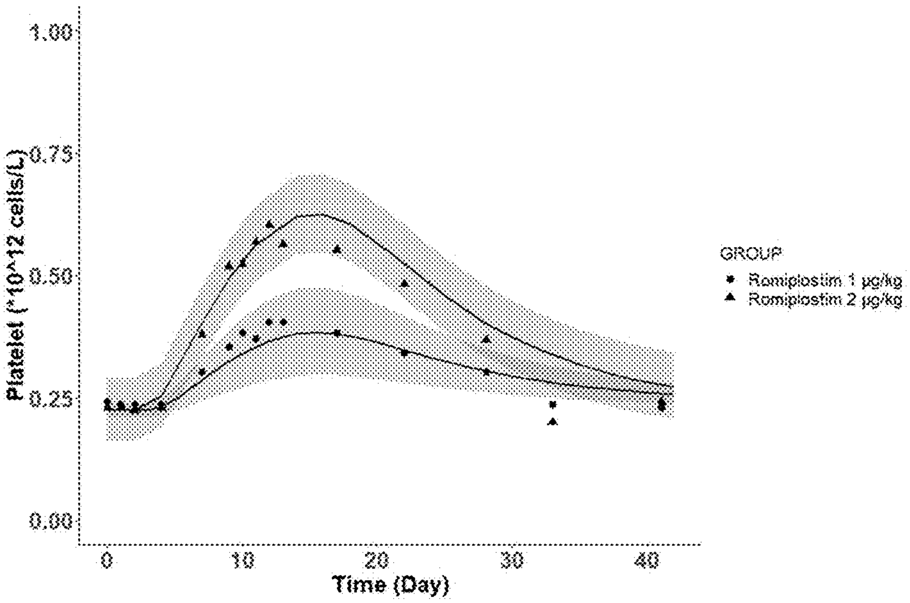
FIGS. 3A-3F. PK/PD model predicted (FIG. 3A) platelets following a single dose of romiplostim 1 or 2 μg/kg SC and Hgb following IV dose of rHuEPO 100 IU/kg TIW (FIG. 3B), SC dose of rHuEPO 100 IU/kg TIW (FIG. 3C), SC dose of rHuEPO 150 IU/kg TIW (FIG. 3D), SC dose of rHuEPO 600 IU/kg QW (FIG. 3E), and SC dose of rHuEPO 60000 IU QW (FIG. 3F) for 4 weeks in healthy subjects. Symbols represent observed platelet and Hgb profiles following romiplostim or rHuEPO treatments digitized from previous reports (Krzyzanski et al., 2005; Ramakrishnan et al., 2004; Wang et al., 2010; Yan et al., 2012). The lines represent PK/PD model-predicted platelet profiles (FIG. 3A) or Hgb profiles (FIGS. 3B-3F) in blood. The shaded area is limited by the 5th and 95th percentiles of the 200 simulated model predictions.
Figure 3B:
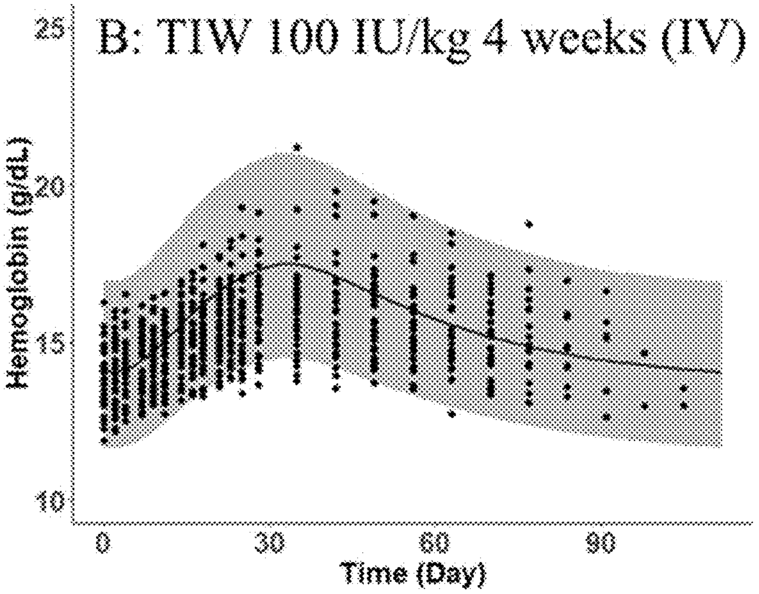
Figure 3C:
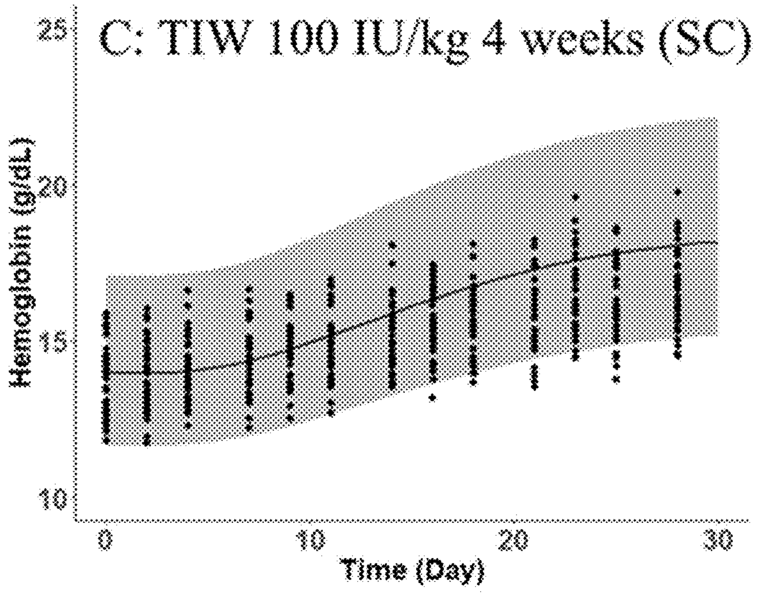
Figure 3D:
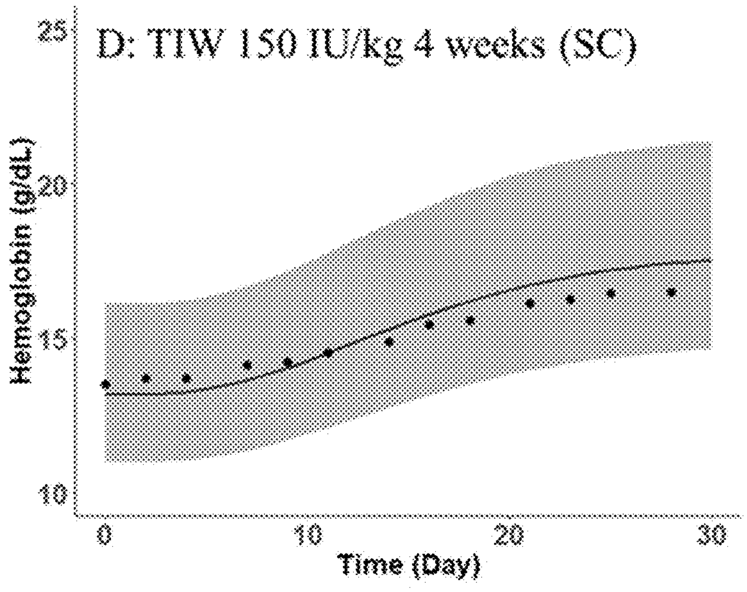
Figure 3E:
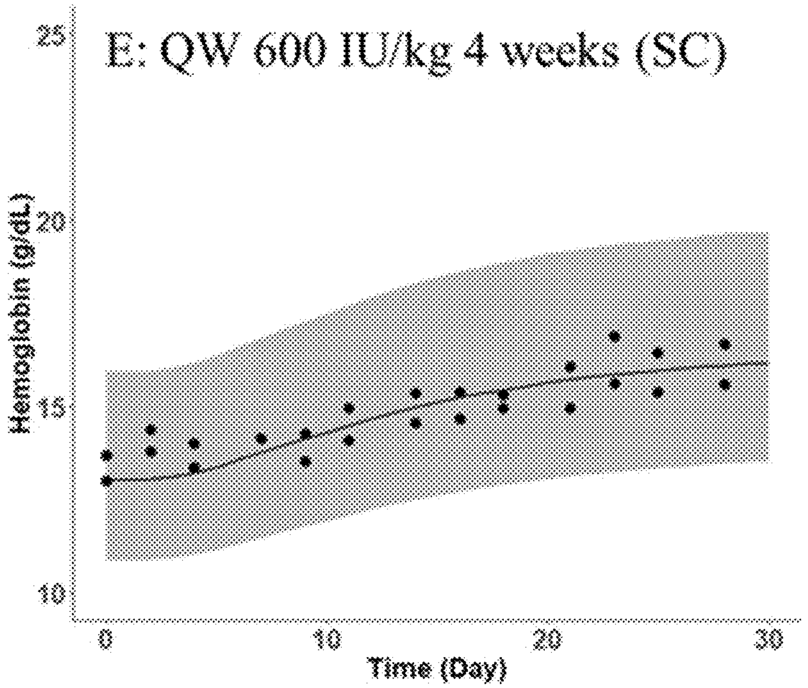
Figure 3F:
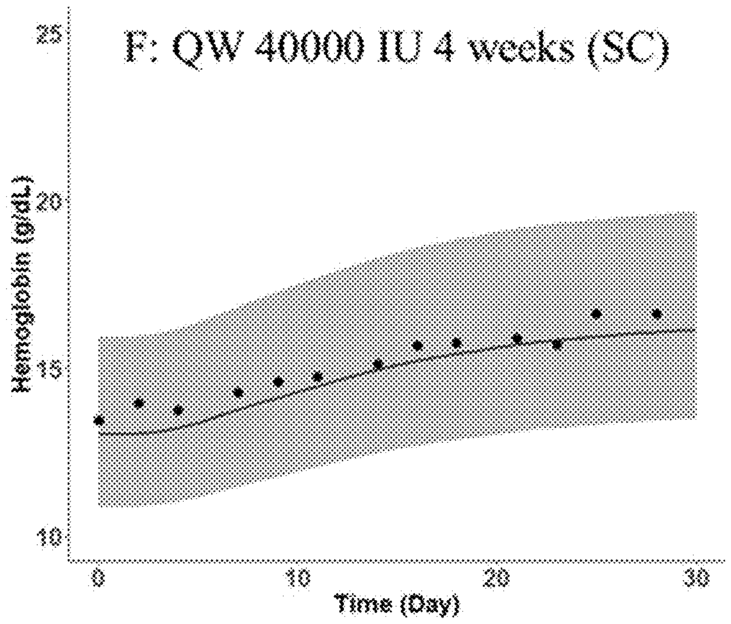

To further examine the model performance and translate the results from rats to humans, allometric scaling was used to extrapolate human PD parameters. The interspecies relationships of $T_{MP}$ and $T_{PLT}$ were described by allometric equations, as shown in FIGS. 2A-2B. A good correlation ($R^2$>0.81) of BW with $T_{MP}$ and $T_{PLT}$ was observed. The PD parameters from the scaling are listed in Table 2 and were retrospectively compared with the physiological values in humans. The scaled $T_{MP}$, $T_{PLT}$, $T_{RET}$, and $T_{RBC}$ were 137.1 h, 10.6 days, 44.8 h, and 119.6 days, respectively, which were close to the physiological values (Harker et al., 2000; Pérez-Ruixo, Krzyzanski, & Hing, 2008; Wang et al., 2010; Yan et al., 2012).

TABLE 2

Estimated PD parameters in healthy rats, scaled PD parameters in healthy subjects using the allometric equation, and observed PD parameters in healthy subjects from the literature (Harker et al., 2000; Krzyzanski et al., 2005; Pérez-Ruixo, et al., 2008; Wang et al., 2010; Yan et al., 2012; Krzyzanski et al., 2013; Gremmel et al., 2016; Corrons, et al., 2021; Zou et al., 2022).

| Parameter | Unit | Estimated value (rat) | Scaled value (humans) | The observed value in humans |
|---|---|---|---|---|
| $T_{MP}$ | h | 47.8 (Krzyzanski et al., 2013) | 137.1 | 142 (Wang et al., 2010) |
| $T_{PLT}$ | day | 6.17 (Krzyzanski et al., 2013) | 10.6 | 8-12 (Harker et al., 2000; Wang et al., 2010) |
| $PLT_0$ | $\times10^{12}$ cells/L | 0.869 (Krzyzanski et al., 2013) | Fixed to human value | 0.23 (Wang et al., 2010; Gremmel et al., 2016) |
| $T_{RET}$ | h | 20 (Zou et al., 2022) | 44.8 | 57.3 (Pérez-Ruixo, et al., 2008; Yan et al., 2012) |
| $T_{RBC}$ | day | 60.8 (Zou et al., 2022) | 119.6 | 120 (Krzyzanski et al., 2005) |
| $RBC_0$ | $\times10^{12}$ cells/L | 7.38 (Zou et al., 2022) | Fixed to human value | 4.4 (Yan et al., 2012; Corrons, et al., 2021) |

Both PK parameters of the two drugs in humans were estimated using the TMDD model, which has been proven to adequately characterize the observed PK profiles of rHuEPO and romiplostim in humans (Wang et al., 2010; Yan et al., 2012; Yan et al., 2020). The PD data of rHuEPO and romiplostim in healthy subjects were digitized from the original articles directly (FIGS. 3A-3F) (Krzyzanski et al., 2005; Ramakrishnan et al., 2004; Wang et al., 2010; Yan et al., 2012). All PK parameters of rHuEPO and romiplostim in humans were maintained identically to those derived from the previous reports (Table 1). As shown in FIGS. 3A-3F, the scaled PK/PD model prediction agreed well with both the observed Hgb and platelet data from rHuEPO- and romiplostim-treated healthy volunteers. In general, the translational mechanism-based PK/PD simulation adequately described the human RBC and platelet responses following repeated IV or SC administration of rHuEPO and a single SC injection of romiplostim. These results provide confidence in the predictive power of the scaled PK/PD model in humans.

Example 3—an Optimal Combination Dosing Regimen in Humans

Figure 4A:
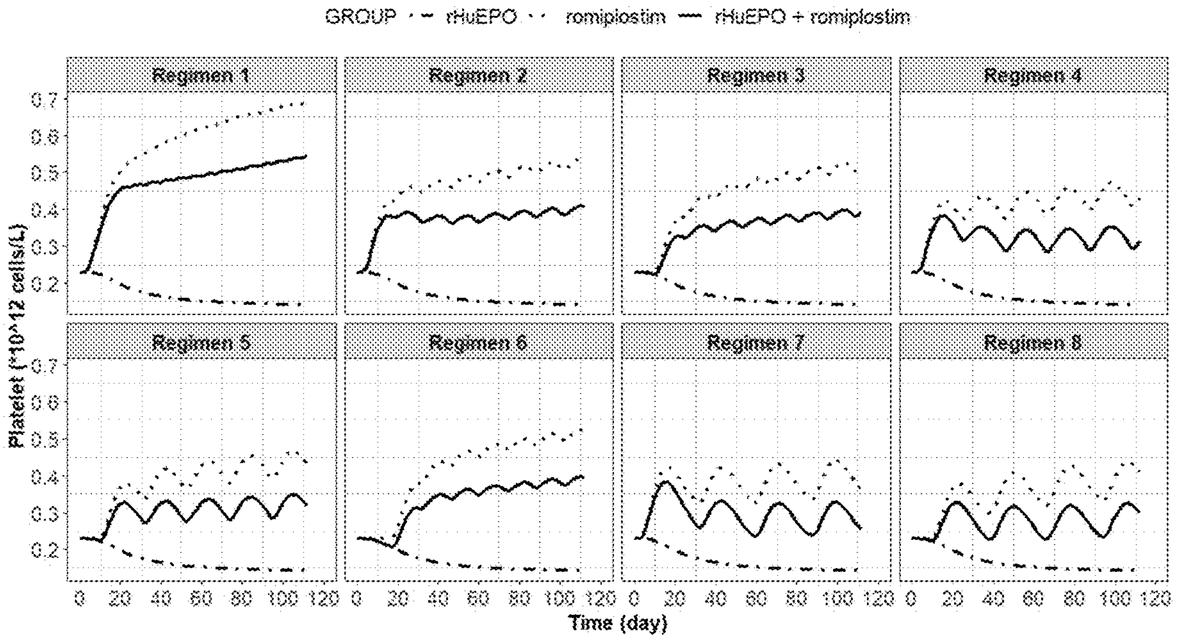
FIGS. 4A-4B. PK/PD model-predicted platelet (FIG. 4A) and Hgb (FIG. 4B) profiles following the different dosing regimens of rHuEPO and romiplostim combination therapy in healthy subjects. The dotted, solid, and two-dash lines are the PD profiles of the rHuEPO monotherapy, rHuEPO+romiplostim combination therapy, and romiplostim monotherapy, respectively.
Figure 4B:
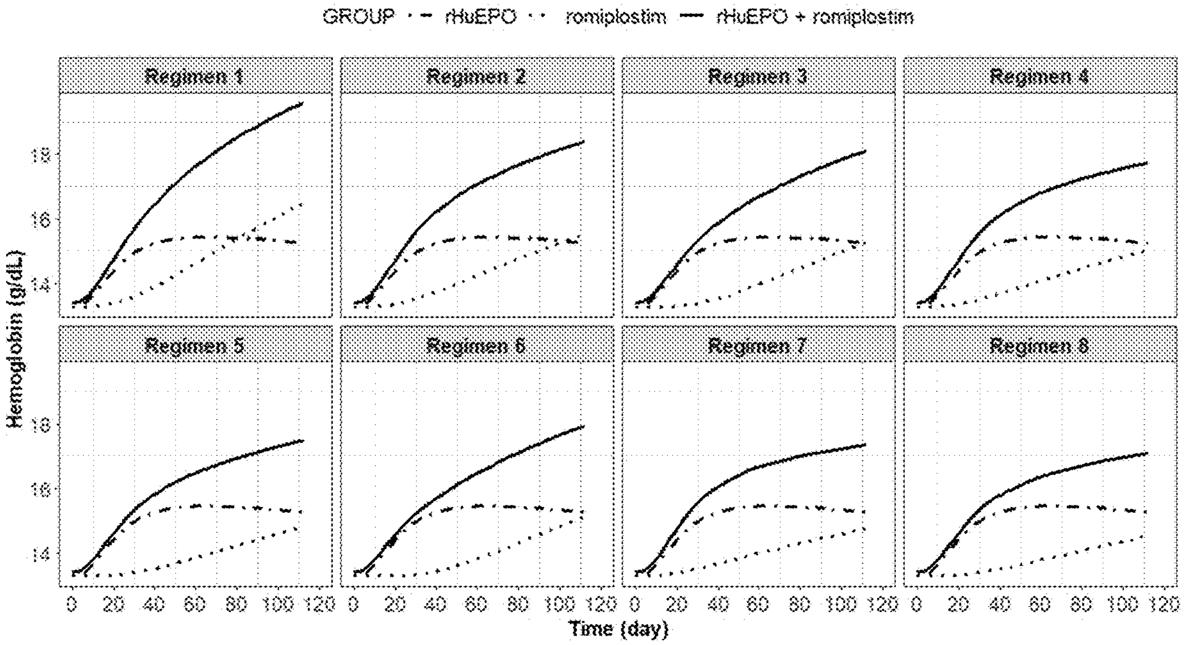
Figure 5A:
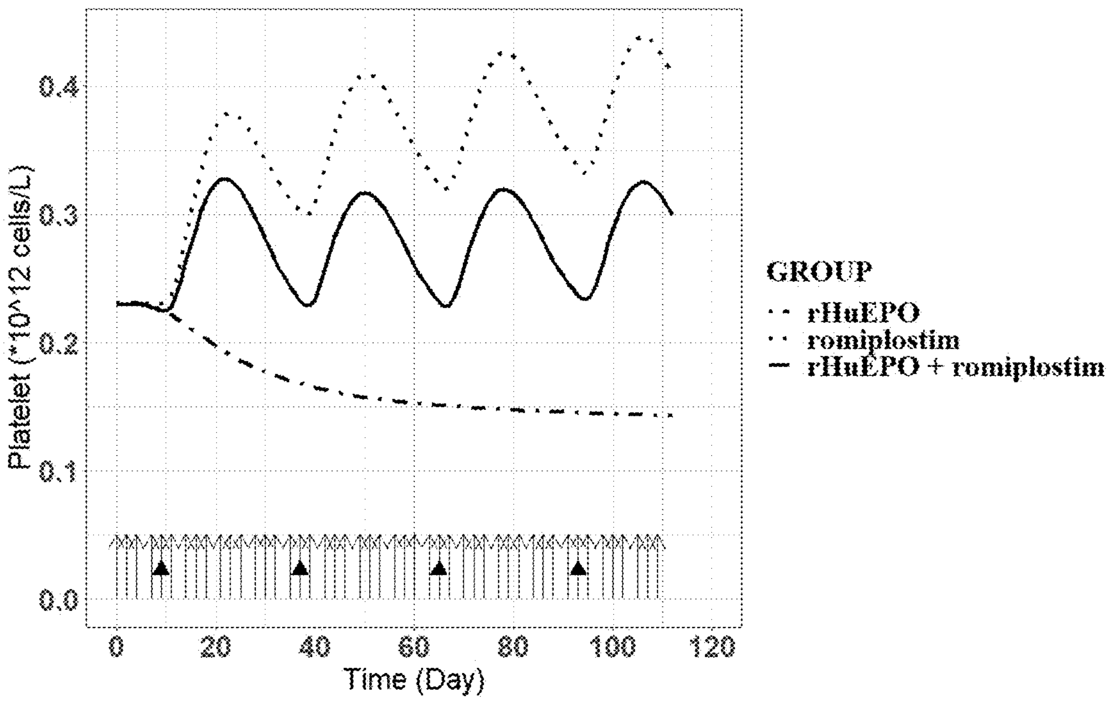
FIGS. 5A-5B. PK/PD model-predicted platelet (FIG. 5A) and Hgb (FIG. 5B) following the recommended dosing regimen 8 (rHuEPO 50 IU/kg TIW+romiplostim 1 μg/kg Q4W from the second week) of rHuEPO and romiplostim combination therapy in healthy subjects. The green solid line is the PD profile of the combination therapy, whereas the red dotted line and the blue two-dash line are the corresponding rHuEPO and romiplostim monotherapy PD profiles, respectively. The arrows represent the dosing events of rHuEPO (long arrow) and romiplostim (short, closed arrow).
Figure 5B:
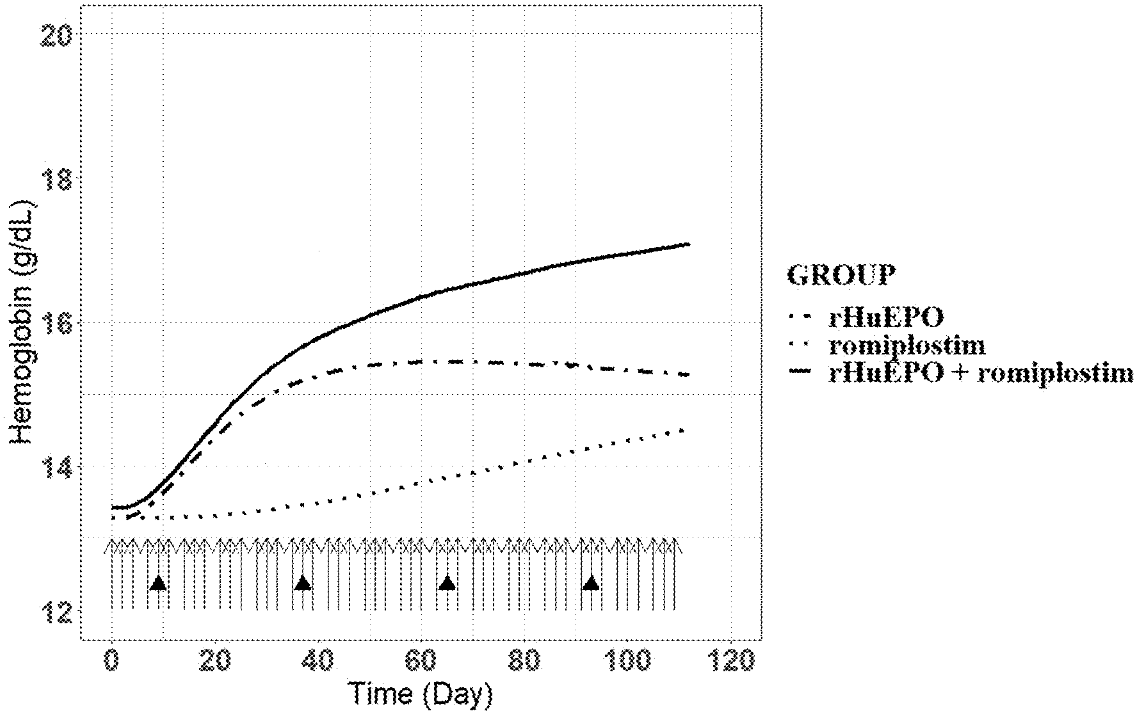

The simulated median Hgb and platelet concentrations under eight dosing regimens of the combination therapy are shown in FIGS. 4A-4B, and the comparison of the simulation results is presented in Table 3. The simulation results showed that the predicted mean Hgb concentration in the rHuEPO monotherapy groups (conventional anemia treatment) reached a peak value of 15.4 g/dL on day 64, and then decreased thereafter although rHuEPO was still being administered. This result suggested EPO hyporesponsiveness, consistent with a previous report (Yan et al., 2012). When combined with romiplostim under different dosing regimens, the Hgb concentration in all combination treatment groups was further increased, which indicated that the combination therapy could correct EPO resistance. However, the platelet count exceeded the normal limit of $0.35\times10^{12}$/L in some dosing regimens (regimens 1, 2, 3, 4, 6, and 7), which was considered unacceptable due to the risk of thrombocytosis. The platelet count was maintained within the normal range in regimens 5 and 8, leading to a recommendation of regimen 8 (EPO 50 IU/kg TIW+romiplostim 1 μg/kg once every 4 weeks [Q4W] from the second week) (FIGS. 5A-5B) for patients, given the efficacy, compliance, and cost-effectiveness.

Example 4 EPO-Resistance Treatment

Our previous studies in anemic CKD rats demonstrated that romiplostim in combination with rHuEPO has great potential to correct EPO resistance (Fan et al., 2022; Zou et al., 2022). Moreover, a mechanism-based PK/PD model was developed, which successfully quantified the interaction between rHuEPO and romiplostim. However, there is a critical gap in translating experimental data into clinical practice. Interspecies allometric scaling is a useful tool for drug development and has been frequently used to predict human PK and PD parameters (Chiou, Robbie, Chung, Wu, & Ma, 1998; Knibbe et al., 2005; Mager et al., 2009; Stevens et al., 2012; van Wijk et al., 2020).

Both rHuEPO and romiplostim are marketed drugs with clinically proven efficacy and safety. Their PK parameters in humans are available and were employed to drive the PD effects directly (Table 1). However, these parameters were estimated using the TMDD model, which is different from our previously developed PK model for rHuEPO and romiplostim in rats. To scale the PD parameters more accurately, the compartmental PK model was adjusted to the MM TMDD model, and the PD parameters were re-estimated. The proposed MM-TMDD PK/PD model (FIG. 1) captured both the PK and PD profiles of romiplostim and rHuEPO after monotherapy and combination therapy, and the re-estimated PD parameters were close to the previous estimation (Table 5) (Fan et al., 2022).

TABLE 5

Model estimates of the fixed- and random-effect PD parameters together with their relative standard errors (RSEs).

| Parameter | Parameter explanation | Unit | Estimate (% RSE) | IIV (% RSE) |
|---|---|---|---|---|
| $T_{MP}$ | Mean lifespan of megakaryocyte cells | h | 37.6 (5.24) | —[a] |
| $T_{PLT}$ | Mean lifespan of platelets | h | 209 (3.57) | —[a] |
| $PLT_0$ | Baseline platelets in blood | $\times 10^{12}$ cells/L | 1.17 (1.30) | 0.0567 (19.9) |
| $T_{RBC}$ | Mean residence time for mature RBCs | h | 998 (3.29) | —[a] |
| $T_{RET}$ | Mean residence time for RETs | h | 50.2 (3.61) | —[a] |
| $RBC_0$ | Baseline RBCs concentration | $\times 10^{12}$ cells/L | 5.65 (0.689) | 0.03 (34.9) |
| KE | First-order rate constant of MEPs differentiate into BFU-E | $\times 10^{-4}$/h | 6.84 (4.30) | —[a] |
| KM | First-order rate constant of MEPs differentiate into MK1 | $\times 10^{-4}$/h | 1.18 (4.91) | —[a] |
| $Smax_{RM1}$ | Maximal stimulus of romiplostim on MEPs | Dimensionless | 1.67 (6.77) | —[a] |
| $Smax_{RM2}$ | Maximal stimulus of romiplostim on MK-committed pathway | Dimensionless | 27.8 (6.58) | —[a] |
| $Smax_{EPO1}$ | Maximal stimulus of rHuEPO on MEPs | Dimensionless | 11.3 (7.01) | —[a] |
| $SC50_{RM}$ | The concentrations of romiplostim that induce a half-maximum effect | ng/mL | 11.9 (7.60) | —[a] |
| $SC50_{EPO}$ | The concentrations of rHuEPO that induce a half-maximum effect | mIU/mL | 46.9 (12.7) | —[a] |
| $Imax_{EPO}$ | Maximal inhibition of rHuEPO on RETs aging rates | Dimensionless | 0.422 (5.97) | —[a] |
| $IC50_{EPO}$ | The concentration of rHuEPO that induces half-maximum inhibition | mIU/mL | 5.59 (9.54) | —[a] |
| MCH | Mean corpuscular hemoglobin | pg/cell | 21.0 (2.77) | —[a] |
| $GAM_1$ | Hill factor on physiological limit | Dimensionless | 1.2 (5.33) | —[a] |
| $GAM_2$ | Hill factor on $SC50_{RM}$ | Dimensionless | 94.2 (6.25) | —[a] |
| $\sigma_{PLT}$ | Proportional error of platelets | Dimensionless | 0.138 (2.58) | —[b] |
| $\sigma_{RBC}$ | Proportional error of RBC | Dimensionless | 0.0843 (2.63) | —[b] |
| $\sigma_{HGB}$ | Additive error of HGB | Dimensionless | 1.23 (2.44) | —[b] |
| $\sigma_{RET2}$ | Proportional error of RET | Dimensionless | 0.575 (4.32) | —[b] |
| OBJ | Objective function value | Dimensionless | −1845 | —[b] |

Note:
The PK parameters are fixed at their estimated values. The RSEs for ω and σ are reported on the approximate standard deviation scale (standard error/variance estimate)/2.
Interindividual variability (IIV) is expressed as the coefficient of variation (%).
σ represents the variance in the residual error.
—[a], did not apply due to no improvement in the goodness of fit.
—[b], not applicable.

Next, allometric scaling was performed and validated based on the PD parameters above and the allometric equation between rats and humans (FIGS. 2A-2B). The scaling of rHuEPO from rats to humans has been performed by others, which was applied in the present study (Woo & Jusko, 2007). The PD parameters of romiplostim, including the megakaryocyte lifespan $T_{MP}$ and platelet lifespan $T_{PLT}$ were scaled. The pharmacologic parameters, including the capacity ($S_{max}$) and sensitivity ($SC_{50}$) of rHuEPO and romiplostim, did not follow allometric principles; these tend to be similar across species because of the receptor density and/or structural homology between species (Mager et al., 2009; Woo & Jusko, 2007). The scaled PD parameters were close to the physiological values in humans (Table 2), which proved that the established PK/PD model was valuable for cross-species extrapolation. The scaled models were externally validated using rHuEPO and romiplostim PD data from healthy subjects, and the results demonstrated the accuracy of the scaled PK/PD model in humans (FIGS. 3A-3F).

Model-based simulations were conducted to optimize the combination dosing regimen and thus guide future clinical trials. The results shown in FIGS. 4A-4B indicate that intensive rHuEPO treatment alone could result in EPO resistance, consistent with previous studies (Yan et al., 2012). The combination of rHuEPO with romiplostim led to a synergistic increase in the Hgb value. However, intensive administration of romiplostim resulted in a platelet count exceeding the normal range ($0.35\times10^{12}$/L), which increased the risk of thrombosis. The results of simulation with regimens 5 and 8 showed that the administration of romiplostim 1 μg/kg Q3W or 1 μg/kg Q4W from the second week was effective in correcting EPO resistance and maintaining the platelet count within a normal range simultaneously. Based on a balance between efficacy, compliance, and cost-effectiveness for patients, regimen 8 (rHuEPO 50 IU/kg TIW+romiplostim 1 μg/kg Q4W from the second week) (FIGS. 5A-5B) is recommended as the starting dose. Moreover, as the current dosing regimen of romiplostim in immune thrombocytopenia patients is 1-10 μg/kg QW, this recommendation provides a huge safety margin for dose escalation during combination treatment to boost efficacy (Bussel et al., 2021).

Interestingly, there are two case reports on the combined usage of romiplostim and darbepoetin, a second-generation ESA with a longer half-life. In one case report, a patient with myelodysplastic syndrome was treated concomitantly with darbepoetin (500 μg Q3W for 3 months, followed by 500 μg Q2W for another 11 months, 300 μg Q3W for another 6 months, and 300 μg Q4W for another 4 months before stopping) and romiplostim (10 μg/kg QW for 9 months) (Prica & Buckstein, 2015). The results of that case were consistent with our preclinical results, and romiplostim was suggested to stimulate the erythroid response in addition to the effects of darbepoetin and a reduced darbepoetin dosage. Meanwhile, the platelet count did not increase during the combined use of darbepoetin and romiplostim (Prica & Buckstein, 2015). Because TPO-RAs have shown efficacy in this patient population (Capecchi et al., 2021), the observation by Prica and Buckstein supports the inhibitory role of darbepoetin on platelets in combination therapy. The other case report showed that the combination of romiplostim and darbepoetin was successfully used as supportive therapy for chemotherapy-associated anemia and thrombocytopenia during induction chemotherapy in a patient with acute lymphoblastic leukemia who wished to avoid blood transfusions due to their beliefs as a Jehovah's Witness (Arora, Gupta, Li, & Sadeghi, 2018).

It should be noted that the actual dosing regimen needs to be adjusted according to the clinical situation. According to the drug label of epoetin, the recommended starting dose for adult patients with CKD is 50-100 U/kg TIW IV or SC, and the IV route is recommended for patients on hemodialysis ("KDOQI Clinical Practice Guideline and Clinical Practice Recommendations for anemia in chronic kidney disease: 2007 update of hemoglobin target," 2007). The model validation results (FIGS. 3A-3F) supported the similar efficacy of the SC dosing regimen. Moreover, the dose of rHuEPO should be adjusted (reduced by 25%) if the Hgb concentration rises rapidly (e.g., >1 g/dL over 2 weeks) to reduce rapid responses. When combined with romiplostim, increases in Hgb should be monitored, and the dose of rHuEPO should be adjusted if Hgb increases too rapidly (>1 g/dL over 2 weeks). Given the dose titration algorithm, the doses of TPO-RAs and ESAs might shift in the same direction during titration to inhibit platelet production, according to the mechanisms of action of the combination therapy.

In summary, the use of interspecies allometric scaling, values of clinical drug-specific and physiological system-specific PK and PD parameters from the literature, and a PD simulation allowed extrapolation of experimental data to humans with a reasonable degree of success. The established PK/PD model was able to predict the PD responses of romiplostim and rHuEPO in both monotherapy and combination therapy in healthy subjects. These data enable a recommendation for an optimal combination dosing regimen to treat EPO resistance.

It should be understood that the examples and embodiments described herein are for illustrative purposes only and that various modifications or changes in light thereof will be suggested to persons skilled in the art and are to be included within the spirit and purview of this application. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

EXEMPLARY EMBODIMENTS

Embodiment 1. A method of treating erythropoiesis-stimulating agents resistant anemia in a subject comprising administering effective amounts of a first composition comprising an erythropoiesis-stimulating agent (ESA) and a second composition comprising a thrombopoietin receptor agonist (TPO-RA), wherein a dose of the ESA administered to the subject is about 0.01 mcg/kg to about 5 mcg/kg.

Embodiment 2. The method of embodiment 1, wherein the subject has chronic kidney disease.

Embodiment 3. The method of embodiment 1, wherein the dose of the ESA administered to the subject is about 0.01 mcg/kg to about 2.50 mcg/kg.

Embodiment 4. The method of embodiment 3, wherein the dose of the ESA administered to the subject is about 0.60 mcg/kg.

Embodiment 5. The method of embodiment 1, wherein a dose of the TPO-RA administered to the subject is about 0.01 μg/kg to about 100 μg/kg.

Embodiment 6. The method of embodiment 5, wherein the dose of the TPO-RA administered to the subject is about 1 μg/kg.

Embodiment 7. The method of embodiment 1, wherein the first composition is administered thrice weekly.

Embodiment 8. The method of embodiment 1, wherein the second composition is administered once every 4 weeks.

Embodiment 9. The method of embodiment 1, wherein a first dose of the second composition is administered about two weeks after a first dose of the first composition.

Embodiment 10. The method of embodiment 1, wherein the TPO-RA is romiplostim.

Embodiment 11. The method of embodiment 1, wherein the ESA is a recombinant human erythropoietin (rHuEPO).

Embodiment 12. The method according to embodiment 1, wherein the first composition and the second composition are administered by intravenous or subcutaneous administration.

Embodiment 13. The method of embodiment 1, wherein the first composition and the second composition further comprise a pharmaceutically acceptable excipient and/or carrier.

REFERENCES

Ait-Oudhia, S., Schermann, J. M., & Krzyzanski, W. (2010). Simultaneous pharmacokinetics/pharmacodynamics modeling of recombinant human erythropoietin upon multiple intravenous dosing in rats. *J Pharmacol Exp Ther,* 334(3), 897-910. doi:10.1124/jpet.110.167304

Arora, N., Gupta, A., Li, H. C., & Sadeghi, N. (2018). Use of platelet and erythroid growth factors during induction chemotherapy for acute lymphoblastic leukaemia in a Jehovah's Witness. *BMJ Case Rep,* 11(1). doi:10.1136/bcr-2018-226497

Babitt, J. L., & Lin, H. Y (2012). Mechanisms of anemia in CKD. *J Am Soc Nephrol,* 23(10), 1631-1634. doi:10.1681/asn.2011111078

Boxenbaum, H. (1982). Interspecies scaling, allometry, physiological time, and the ground plan of pharmacokinetics. *J Pharmacokinet Biopharm,* 10(2), 201-227. doi:10.1007/bf01062336

Bussel, J. B., Soff, G., Balduzzi, A., Cooper, N., Lawrence, T., & Semple, J. W. (2021). A Review of Romiplostim Mechanism of Action and Clinical Applicability. *Drug Des Devel Ther,* 15, 2243-2268. doi:10.2147/dddt.S299591

Capecchi, M., Serpenti, F., Giannotta, J., Pettine, L., Reda, G., Martinelli, I., . . . Fattizzo, B. (2021). Off-Label Use of Thrombopoietin Receptor Agonists: Case Series and Review of the Literature. *Front Oncol,* 11, 680411. doi:10.3389/fonc.2021.680411

Chiou, W. L., Robbie, G., Chung, S. M., Wu, T. C., & Ma, C. (1998). Correlation of plasma clearance of 54 extensively metabolized drugs between humans and rats: mean allometric coefficient of 0.66. *Pharm Res,* 15(9), 1474-1479. doi:10.1023/a:1011974226596

Corrons, J. L. V, Casafont, L. B., & Frasnedo, E. F. (2021). Concise review: how do red blood cells born, live, and die? *Ann Hematol,* 100(10), 2425-2433. doi:10.1007/s00277-021-04575-z Costa, E., Rocha, S., Rocha-Pereira, P., Nascimento, H., Castro, E., Miranda, V., . . . Santos-Silva, A. (2008). Neutrophil activation and resistance to recombinant human erythropoietin therapy in hemodialysis patients. *Am J Nephrol,* 28(6), 935-940. doi:10.1159/000142147

Dedrick, R. L. (1973). Animal scale-up. *J Pharmacokinet Biopharm,* 1(5), 435-461. doi:10.1007/bf01059667

Elliott, S. (2011). Erythropoiesis-stimulating agents. *Cancer Treat Res,* 157, 55-74. doi:10.1007/978-1-4419-7073-2_4

Fan, X., Krzyzanski, W., Wong, R. S. M., & Yan, X. (2022). Fate determination role of erythropoietin and romiplostim in the lineage commitment of hematopoietic progenitors. *J Pharmacol Exp Ther.* doi:10.1124/jpet.122.001130

Fukuma, S., Yamaguchi, T., Hashimoto, S., Nakai, S., Iseki, K., Tsubakihara, Y, & Fukuhara, S. (2012). Erythropoiesis-stimulating agent responsiveness and mortality in hemodialysis patients: results from a cohort study from the dialysis registry in Japan. *Am J Kidney Dis,* 59(1), 108-116. doi:10.1053/j.ajkd.2011.07.014

Gremmel, T., Frelinger, A. L., 3rd, & Michelson, A. D. (2016). Platelet Physiology. *Semin Thromb Hemost,* 42(3), 191-204. doi:10.1055/s-0035-1564835

Gutti, U., Pasupuleti, S. R., Sahu, I., Kotipalli, A., Undi, R. B., Kandi, R., . . . Gutti, R. K. (2016). Erythropoietin and thrombopoietin mimetics: Natural alternatives to erythrocyte and platelet disorders. *Crit Rev Oncol Hematol,* 108, 175-186. doi:10.1016/j.critrevonc.2016.11.002

Harker, L. A., Roskos, L. K., Marzec, U. M., Carter, R. A., Cherry, J. K., Sundell, B., . . . Sheridan, W. (2000). Effects of megakaryocyte growth and development factor on platelet production, platelet life span, and platelet function in healthy human volunteers. *Blood,* 95(8), 2514-2522.

Icardi, A., Paoletti, E., De Nicola, L., Mazzaferro, S., Russo, R., & Cozzolino, M. (2013). Renal anaemia and EPO hyporesponsiveness associated with vitamin D deficiency: the potential role of inflammation. *Nephrol Dial Transplant,* 28(7), 1672-1679. doi:10.1093/ndt/gft021

Jolling, K., Perez Ruixo, J. J., Hemeryck, A., Vermeulen, A., & Greway, T. (2005). Mixed-effects modelling of the interspecies pharmacokinetic scaling of pegylated human erythropoietin. *Eur J Pharm Sci,* 24(5), 465-475. doi:10.1016/j.ejps.2005.01.002

Kainz, A., Mayer, B., Kramar, R., & Oberbauer, R. (2010). Association of ESA hyporesponsiveness and haemoglobin variability with mortality in haemodialysis patients. *Nephrol Dial Transplant,* 25(11), 3701-3706. doi:10.1093/ndt/gfq287

KDOQI Clinical Practice Guideline and Clinical Practice Recommendations for anemia in chronic kidney disease: 2007 update of hemoglobin target. (2007). *Am J Kidney Dis,* 50(3), 471-530. doi:10.1053/j.ajkd.2007.06.008

Kilpatrick, R. D., Critchlow, C. W., Fishbane, S., Besarab, A., Stehman-Breen, C., Krishnan, M., & Bradbury, B. D. (2008). Greater epoetin alfa responsiveness is associated with improved survival in hemodialysis patients. *Clin J Am Soc Nephrol,* 3(4), 1077-1083. doi:10.2215/cjn.04601007

Knibbe, C. A., Zuideveld, K. P., Aarts, L. P., Kuks, P. F., & Danhof, M. (2005). Allometric relationships between the pharmacokinetics of propofol in rats, children and adults. *Br J Clin Pharmacol,* 59(6), 705-711. doi:10.1111/j.1365-2125.2005.02239.x Krzyzanski, W., Jusko, W. J., Wacholtz, M. C., Minton, N., & Cheung, W. K. (2005). Pharmacokinetic and pharmacodynamic modeling of recombinant human erythropoietin after multiple subcutaneous doses in healthy subjects. *Eur J Pharm Sci,* 26(3-4), 295-306. doi:10.1016/j.ejps.2005.06.010

Krzyzanski, W., Ramakrishnan, R., & Jusko, W. J. (1999). Basic pharmacodynamic models for agents that alter production of natural cells. *J Pharmacokinet Biopharm,* 27(5), 467-489. doi:10.1023/a:1023249813106

Krzyzanski, W., Sutjandra, L., Perez-Ruixo, J. J., Sloey, B., Chow, A. T., & Wang, Y M. (2013). Pharmacokinetic and pharmacodynamic modeling of romiplostim in animals. *Pharm Res,* 30(3), 655-669. doi:10.1007/s11095-012-0894-2

Mager, D. E., Woo, S., & Jusko, W. J. (2009). Scaling pharmacodynamics from in vitro and preclinical animal studies to humans. *Drug Metab Pharmacokinet,* 24(1), 16-24. doi:10.2133/dmpk.24.16

Perez-Ruixo, J. J., Krzyzanski, W., & Hing, J. (2008). Pharmacodynamic analysis of recombinant human erythropoietin effect on reticulocyte production rate and age distribution in healthy subjects. *Clin Pharmacokinet,* 47(6), 399-415. doi:10.2165/00003088-200847060-00004

Prica, A., & Buckstein, R. (2015). Myelodysplastic syndrome successfully treated with adalimumab. *J Clin Oncol,* 33(2), e4-6. doi:10.1200/JCO.2013.49.4948

Ramakrishnan, R., Cheung, W. K., Wacholtz, M. C., Minton, N., & Jusko, W. J. (2004). Pharmacokinetic and pharmacodynamic modeling of recombinant human erythropoietin after single and multiple doses in healthy volunteers. *J Clin Pharmacol,* 44(9), 991-1002. doi:10.1177/0091270004268411

Santos, P. R., Melo, A. D., Lima, M. M., Negreiros, I. M., Miranda, J. S., Pontes, L. S., . . . Da Silva Costa, A. (2011). Mortality risk in hemodialysis patients according to anemia control and erythropoietin dosing. *Hemodial Int,* 15(4), 493-500. doi:10.1111/j.1542-4758.2011.00607.x Stevens, J., Ploeger, B. A., Hammarlund-Udenaes, M., Osswald, G., van der Graaf, P. H., Danhof, M., & de Lange, E. C. (2012). Mechanism-based PK-PD model for the prolactin biological system response following an acute dopamine inhibition challenge: quantitative extrapolation to humans. *J Pharmacokinet Pharmacodyn,* 39(5), 463-477. doi:10.1007/s10928-012-9262-4

Suttorp, M. M., Hoekstra, T., Rotmans, J. I., Ott, I., Mittelman, M., Krediet, R. T., & Dekker, F. W. (2013). Erythropoiesis-stimulating agent resistance and mortality in hemodialysis and peritoneal dialysis patients. *BMC Nephrol,* 14, 200. doi:10.1186/1471-2369-14-200 van Wijk, R. C., Hu, W., Dijkema, S. M., van den Berg, D. J., Liu, J., Bahi, R., . . . Krekels, E. H. J. (2020). Anti-tuberculosis effect of isoniazid scales accurately from zebrafish to humans. *Br J Pharmacol,* 177(24), 5518-5533. doi:10.1111/bph.15247 Wang, Y M., Krzyzanski, W., Doshi, S., Xiao, J. J., Perez-Ruixo, J. J., & Chow, A. T. (2010).

Pharmacodynamics-mediated drug disposition (PDMDD) and precursor pool lifespan model for single dose of romiplostim in healthy subjects. *Aaps j,* 12(4), 729-740. doi:10.1208/s12248-010-9234-9

Woo, S., & Jusko, W. J. (2007). Interspecies comparisons of pharmacokinetics and pharmacodynamics of recombinant human erythropoietin. *Drug Metab Dispos,* 35(9), 1672-1678. doi:10.1124/dmd.107.015248

Yan, X., Ait-Oudhia, S., & Krzyzanski, W. (2013). Erythropoietin-induced erythroid precursor pool depletion causes erythropoietin hyporesponsiveness. *Pharm Res,* 30(4), 1026-1036. doi:10.1007/s11095-012-0938-7

Yan, X., Lowe, P. J., Fink, M., Berghout, A., Balser, S., & Krzyzanski, W. (2012). Population pharmacokinetic and pharmacodynamic model-based comparability assessment of a recombinant human Epoetin Alfa and the Biosimilar HX575. *J Clin Pharmacol,* 52(11), 1624-1644. doi:10.1177/0091270011421911

Yan, X., Ruixo, J. J. P., & Krzyzanski, W. (2020). Dose Correction for a Michaelis-Menten Approximation of a Target-Mediated Drug Disposition Model with a Multiple Intravenous Dosing Regimens. *Aaps j,* 22(2), 30. doi:10.1208/s12248-019-0410-2

Zhang, Y, Thamer, M., Kaufman, J. S., Cotter, D. J., & Hernin, M. A. (2011). High doses of epoetin do not lower mortality and cardiovascular risk among elderly hemodialysis patients with diabetes. *Kidney Int,* 80(6), 663-669. doi:10.1038/ki.2011.188

Zou, H., Xu, P., Wong, R. S. M., & Yan, X. (2022). A Novel Combination Therapy of Erythropoietin and Thrombopoietin to Treat Erythropoietin-Resistance anemia. *Pharm Res,* 39(6), 1249-1265. doi:10.1007/s11095-022-03304-z

We claim:

1. A method of treating erythropoiesis-stimulating agents resistant anemia in a subject comprising administering effective amounts of a first composition comprising an erythropoiesis-stimulating agent (ESA) and a second composition comprising a thrombopoietin receptor agonist (TPO-RA), wherein a dose of the ESA administered to the subject is about 0.01 mcg/kg to about 5 mcg/kg.

2. The method of claim 1, wherein the subject has chronic kidney disease.

3. The method of claim 1, wherein the dose of the ESA administered to the subject is about 0.01 mcg/kg to about 2.50 mcg/kg.

4. The method of claim 3, wherein the dose of the ESA administered to the subject is about 0.60 mcg/kg.

5. The method of claim 1, wherein a dose of the TPO-RA administered to the subject is about 0.01 μg/kg to about 100 μg/kg.

6. The method of claim 5, wherein the dose of the TPO-RA administered to the subject is about 1 μg/kg.

7. The method of claim 1, wherein the first composition is administered thrice weekly.

8. The method of claim 1, wherein the second composition is administered once every 4 weeks.

9. The method of claim 1, wherein a first dose of the second composition is administered about two weeks after a first dose of the first composition.

10. The method of claim 1, wherein the TPO-RA is romiplostim.

11. The method of claim 1, wherein the ESA is a recombinant human erythropoietin (rHuEPO).

12. The method according to claim 1, wherein the first composition and the second composition are administered by intravenous or subcutaneous administration.

13. The method of claim 1, wherein the first composition and the second composition further comprise a pharmaceutically acceptable excipient and/or carrier.

* * * * *